US009039780B2

(12) United States Patent
Forsell

(10) Patent No.: US 9,039,780 B2
(45) Date of Patent: May 26, 2015

(54) HIP JOINT DEVICE, SYSTEM AND METHOD

(76) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 13/383,281

(22) PCT Filed: Jul. 12, 2010

(86) PCT No.: PCT/SE2010/050811
§ 371 (c)(1),
(2), (4) Date: Jan. 10, 2012

(87) PCT Pub. No.: WO2011/005192
PCT Pub. Date: Jan. 13, 2011

(65) Prior Publication Data
US 2012/0116534 A1   May 10, 2012

Related U.S. Application Data

(60) Provisional application No. 61/229,738, filed on Jul. 30, 2009, provisional application No. 61/229,796,
(Continued)

(30) Foreign Application Priority Data

| Jul. 10, 2009 | (SE) | 0900957 |
| Jul. 10, 2009 | (SE) | 0900958 |
| Jul. 10, 2009 | (SE) | 0900959 |
| Jul. 10, 2009 | (SE) | 0900960 |
| Jul. 10, 2009 | (SE) | 0900962 |
| Jul. 10, 2009 | (SE) | 0900963 |
| Jul. 10, 2009 | (SE) | 0900965 |
| Jul. 10, 2009 | (SE) | 0900966 |
| Jul. 10, 2009 | (SE) | 0900968 |
| Jul. 10, 2009 | (SE) | 0900969 |
| Jul. 10, 2009 | (SE) | 0900970 |
| Jul. 10, 2009 | (SE) | 0900972 |
| Jul. 10, 2009 | (SE) | 0900973 |
| Jul. 10, 2009 | (SE) | 0900974 |
| Jul. 10, 2009 | (SE) | 0900976 |
| Jul. 10, 2009 | (SE) | 0900978 |
| Jul. 10, 2009 | (SE) | 0900981 |
| Jul. 10, 2009 | (SE) | 0900984 |

(51) Int. Cl.
*A61F 2/36* (2006.01)
(Continued)

(52) U.S. Cl.
CPC ......... *A61F 2/3603* (2013.01); *A61B 17/00491* (2013.01); *A61B 17/1617* (2013.01);
(Continued)

(58) Field of Classification Search
USPC ................... 623/22.11–22.2, 22.21–22.46, 623/23.35–23.37, 19.11–19.14, 623/22.15–22.19
See application file for complete search history.

(56) References Cited

U.S. PATENT DOCUMENTS

| 5,549,704 A | 8/1996 | Sutter |
| 6,482,237 B2 | 11/2002 | Mosseri |

(Continued)

FOREIGN PATENT DOCUMENTS

WO   WO 2009/068011   6/2009

OTHER PUBLICATIONS

International Search Report for PCT/SE2010/050811, mailed Oct. 21, 2010.

*Primary Examiner* — Bruce E Snow
*Assistant Examiner* — Brian Dukert

(57) ABSTRACT

An implantable medical device for implantation in a hip joint of a human patient is provided. The medical device comprises: at least one artificial hip joint surface adapted to replace at least the surface of at least one of the caput femur and acetabulum. At least one artificial hip joint surface comprises: a positioning hole with at least one opening in said at least one artificial hip joint surface. The hole is adapted to be placed and dimensioned such that the medical device is adapted to be fitted using a positioning shaft and at least partly surround the shaft, for positioning the at least one artificial hip joint surface in a desired position in the hip joint. The hole is adapted to be fitted using the positioning shaft, when the shaft is stabilized and placed in at least one of the femoral bone and the pelvic bone for positioning said medical device inside the hip joint.

11 Claims, 25 Drawing Sheets

Related U.S. Application Data filed on Jul. 30, 2009, provisional application No. 61/229,789, filed on Jul. 30, 2009, provisional application No. 61/229,786, filed on Jul. 30, 2009, provisional application No. 61/229,778, filed on Jul. 30, 2009, provisional application No. 61/229,767, filed on Jul. 30, 2009, provisional application No. 61/229,761, filed on Jul. 30, 2009, provisional application No. 61/229,755, filed on Jul. 30, 2009, provisional application No. 61/229,752, filed on Jul. 30, 2009, provisional application No. 61/229,751, filed on Jul. 30, 2009, provisional application No. 61/229,748, filed on Jul. 30, 2009, provisional application No. 61/229,747, filed on Jul. 30, 2009, provisional application No. 61/229,746, filed on Jul. 30, 2009, provisional application No. 61/229,745, filed on Jul. 30, 2009, provisional application No. 61/229,743, filed on Jul. 30, 2009, provisional application No. 61/229,739, filed on Jul. 30, 2009, provisional application No. 61/229,738, filed on Jul. 30, 2009.

(51) Int. Cl.
| | | |
|---|---|---|
| A61B 17/16 | (2006.01) | |
| *A61B 17/56* | (2006.01) | |
| *A61F 2/32* | (2006.01) | |
| A61B 17/00 | (2006.01) | |
| A61F 2/46 | (2006.01) | |
| A61F 2/30 | (2006.01) | |
| A61F 2/34 | (2006.01) | |
| A61B 17/02 | (2006.01) | |

(52) U.S. Cl.
CPC ......... *A61B17/1666* (2013.01); *A61B 17/1668* (2013.01); *A61B 17/56* (2013.01); *A61F 2/32* (2013.01); *A61F 2/3609* (2013.01); *A61F 2/4607* (2013.01); *A61F 2/4609* (2013.01); *A61F 2002/30673* (2013.01); *A61F 2002/30754* (2013.01); *A61F 2002/3233* (2013.01); *A61F 2002/3241* (2013.01); *A61F 2002/342* (2013.01); *A61F 2002/3487* (2013.01); *A61F 2002/3495* (2013.01); *A61F 2002/3615* (2013.01); *A61F 2002/464* (2013.01); *A61B 2017/0275* (2013.01)

(56) References Cited

U.S. PATENT DOCUMENTS

2008/0109085 A1    5/2008   Tulkis et al.
2008/0177395 A1*  7/2008   Stinnette .................... 623/20.22

* cited by examiner

A - A

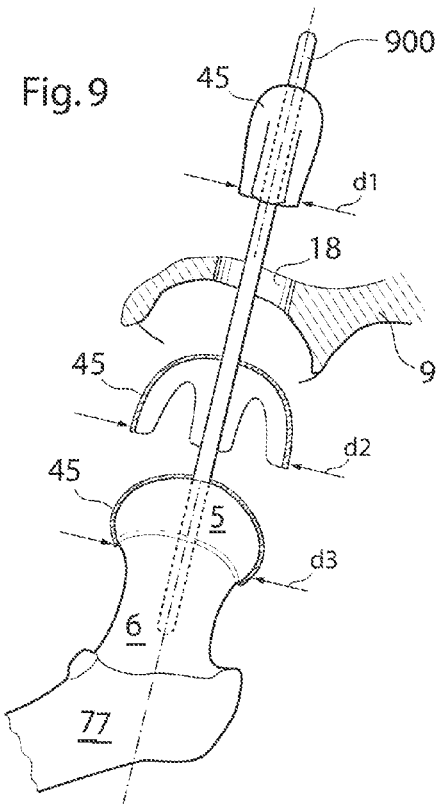
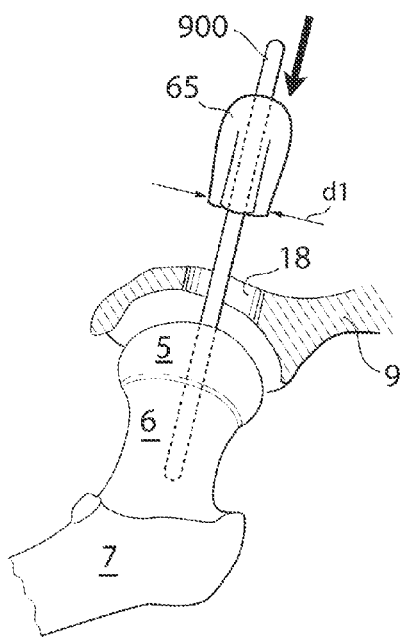
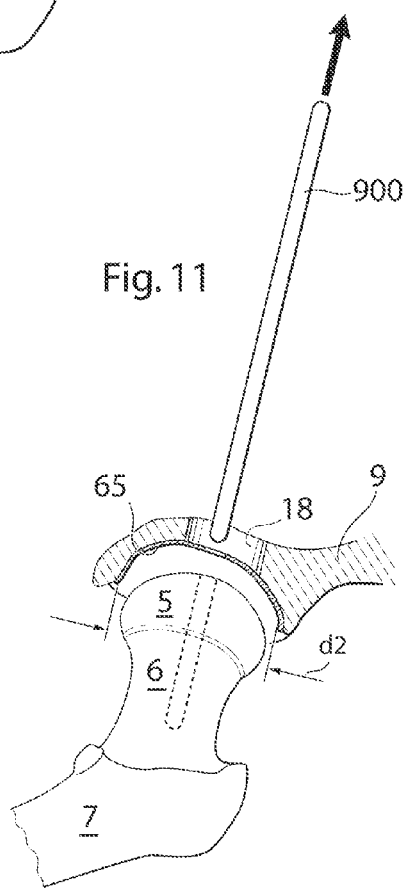
Fig. 9
Fig. 10
Fig. 11

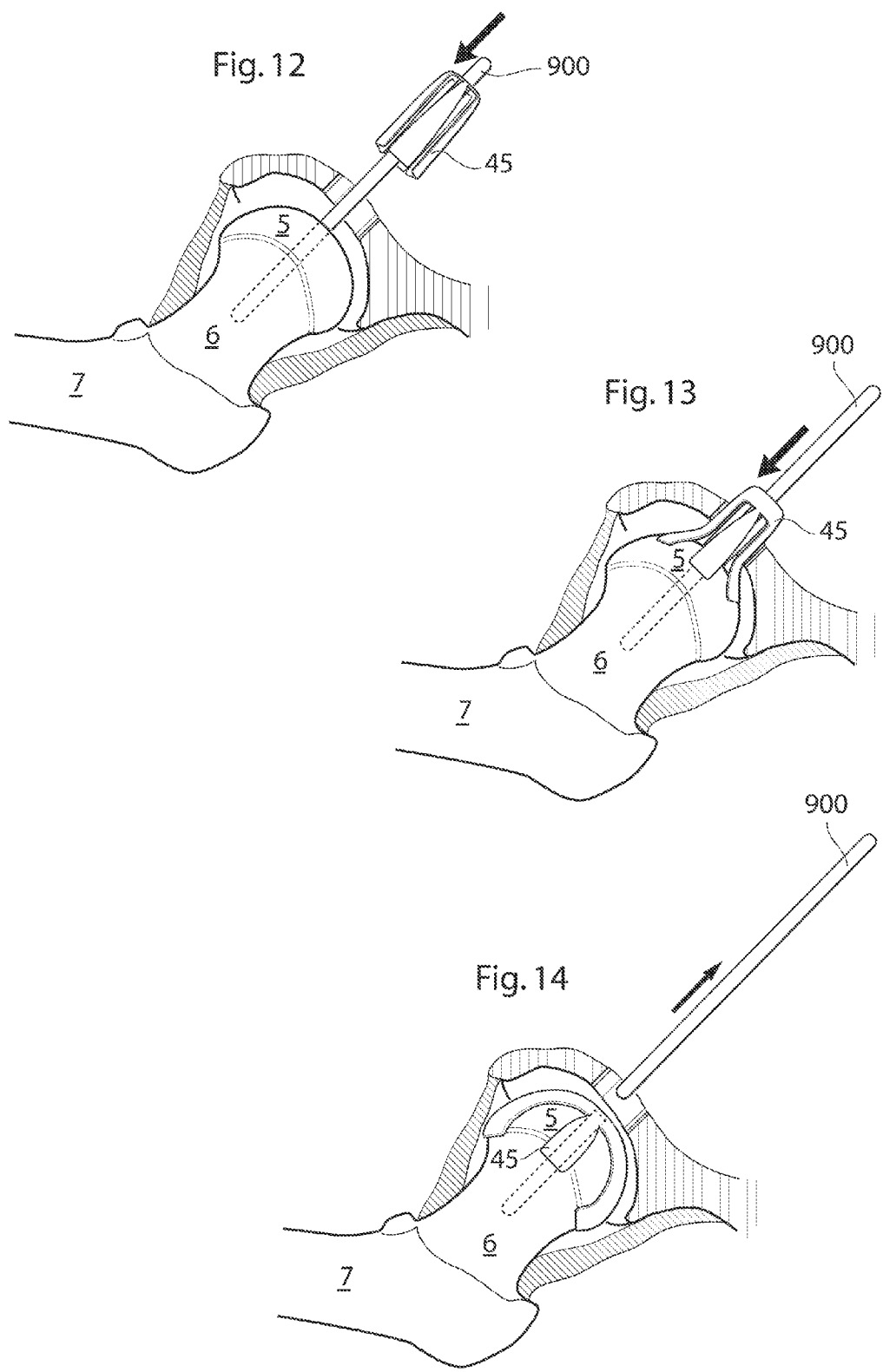

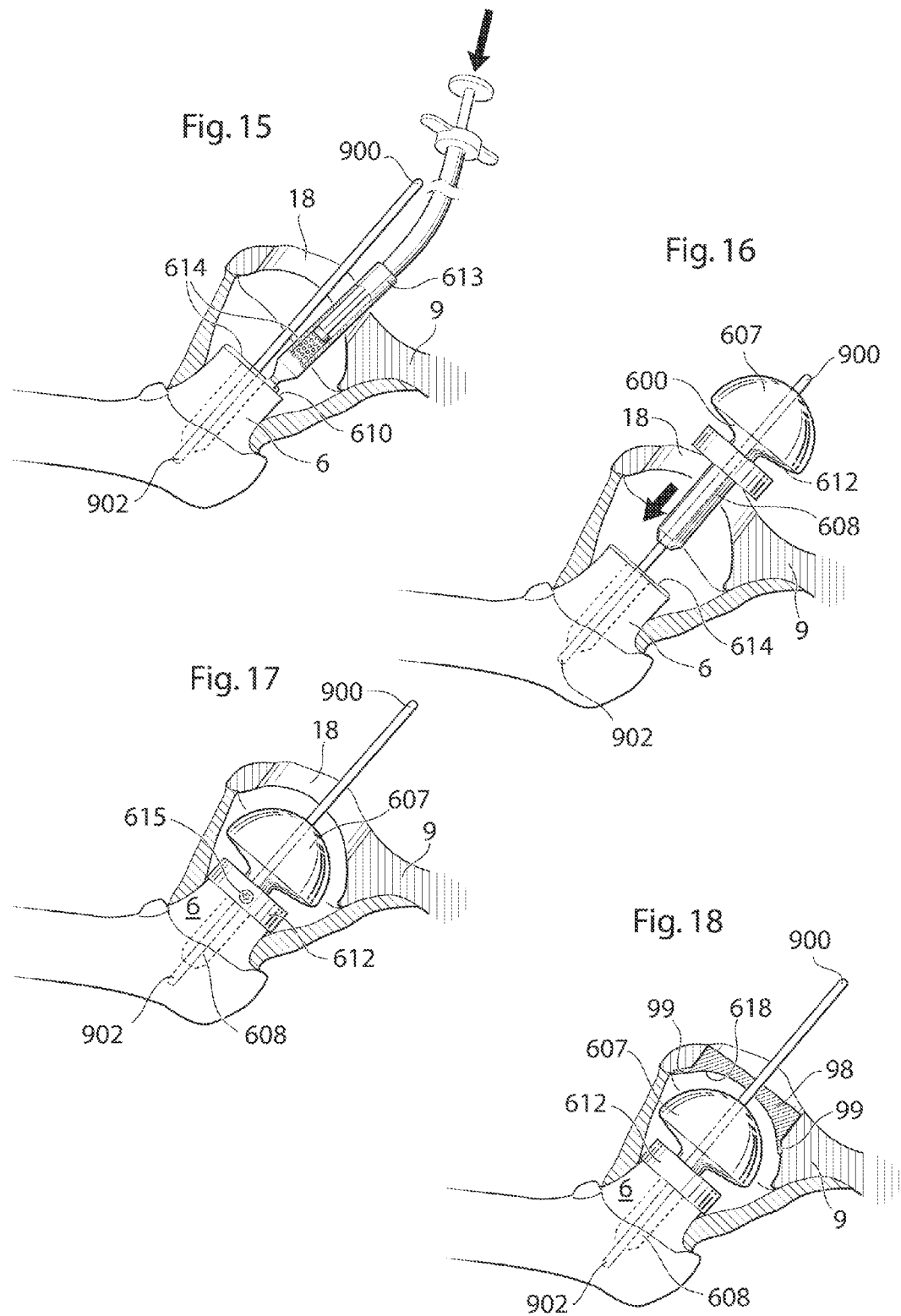

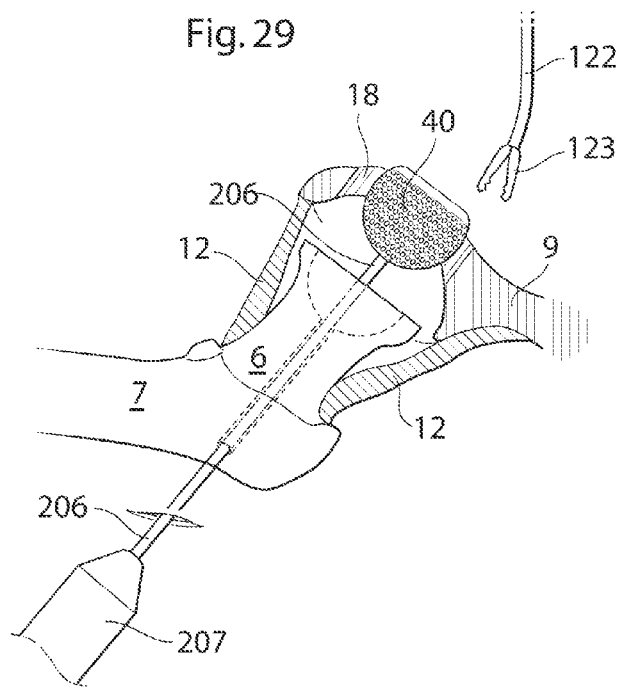
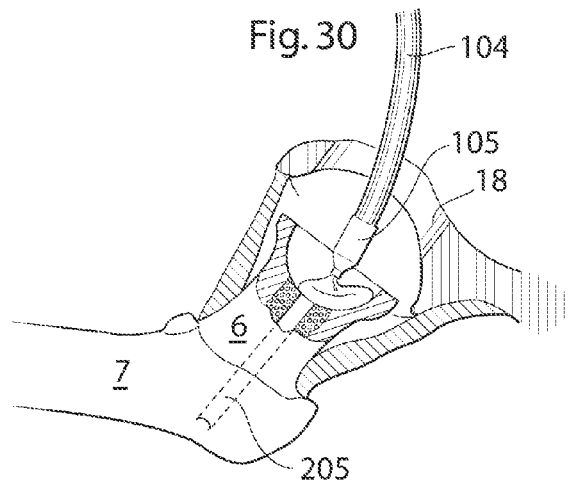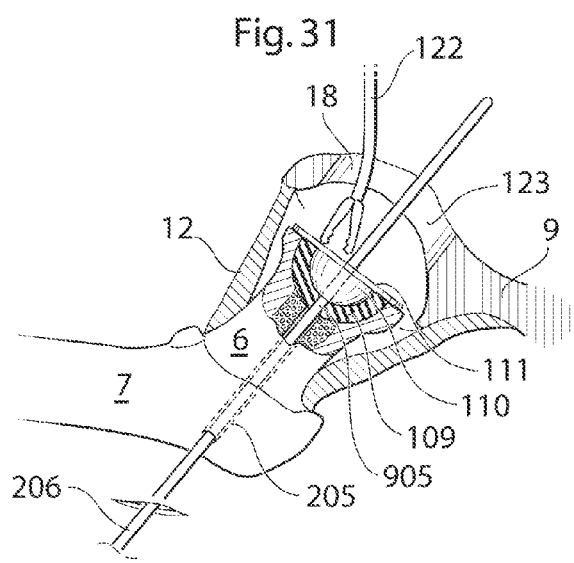

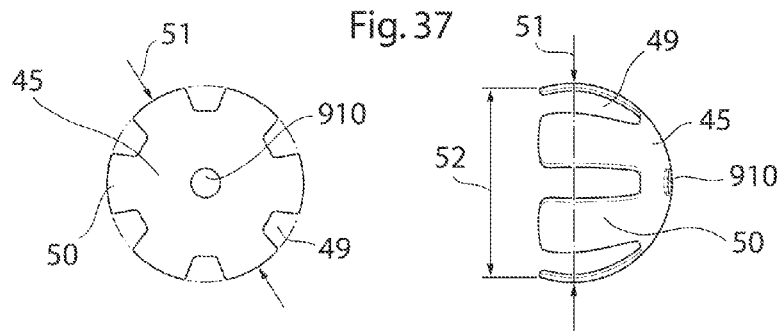
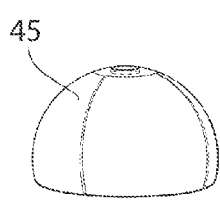
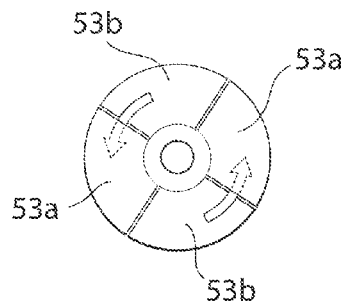
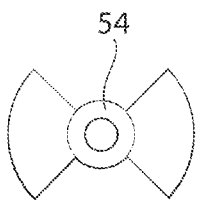
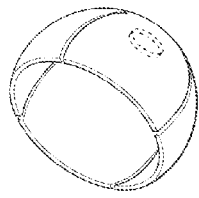
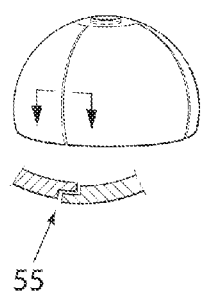
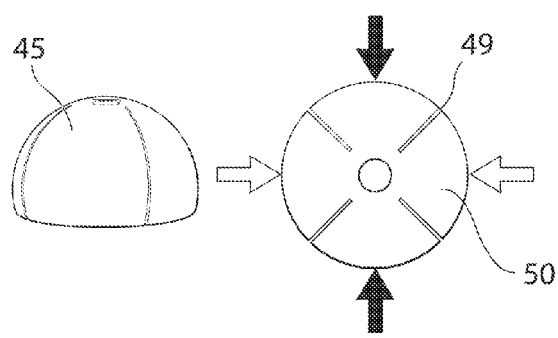
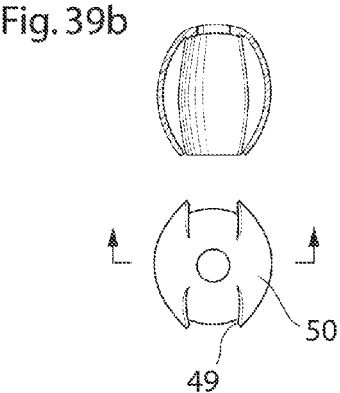

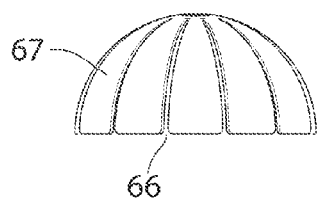
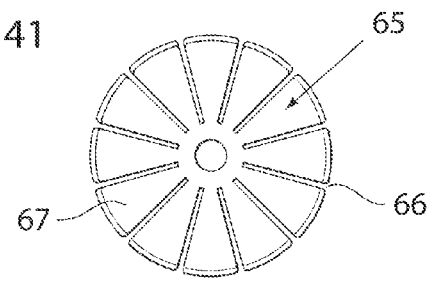
Fig. 41
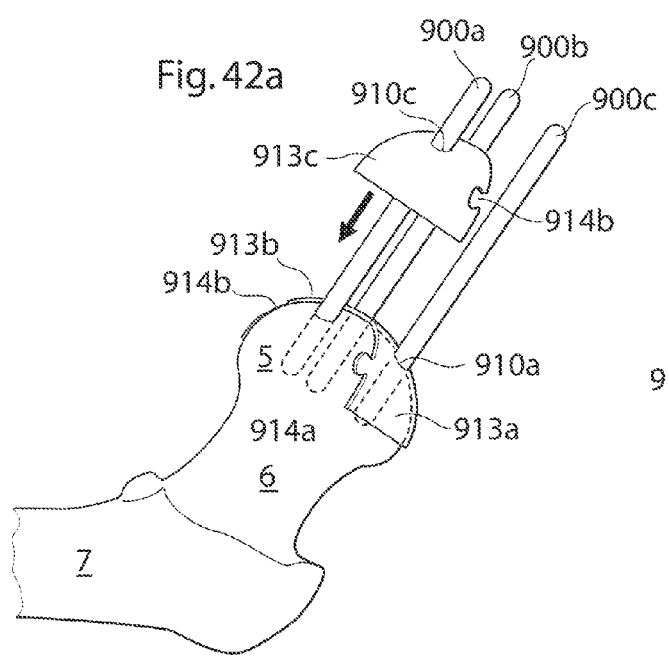
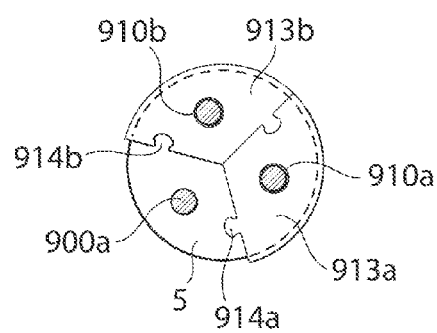
Fig. 42a
Fig. 42b
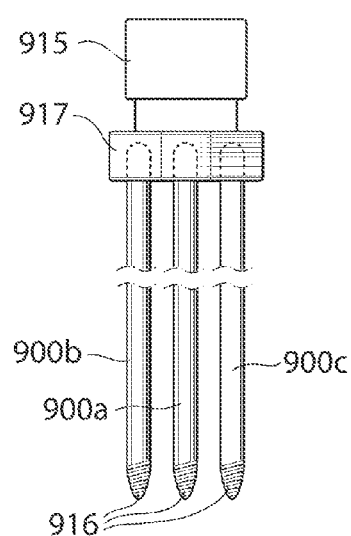
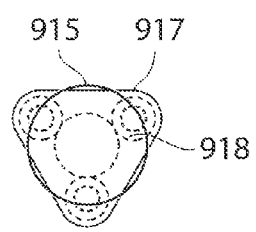
Fig. 43a
Fig. 43b

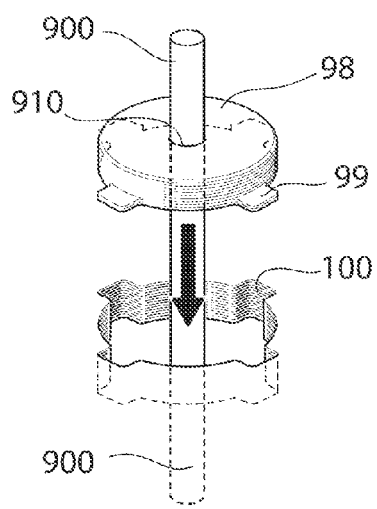
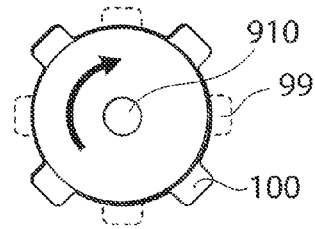
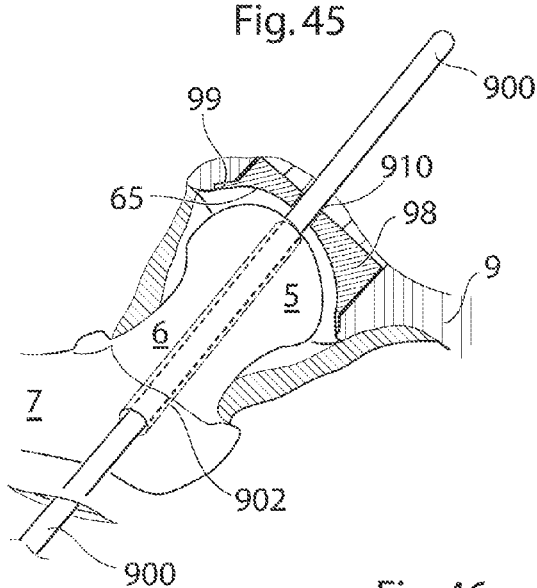
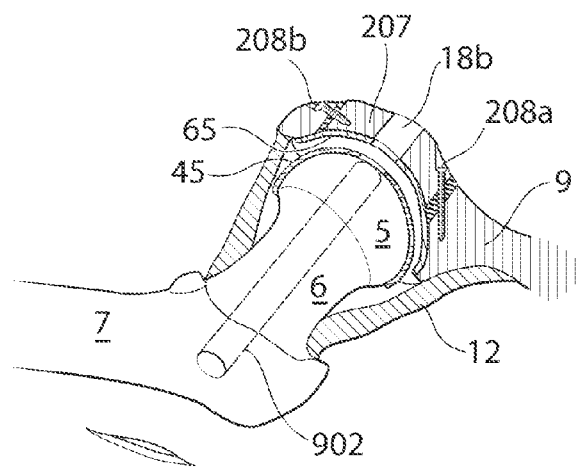

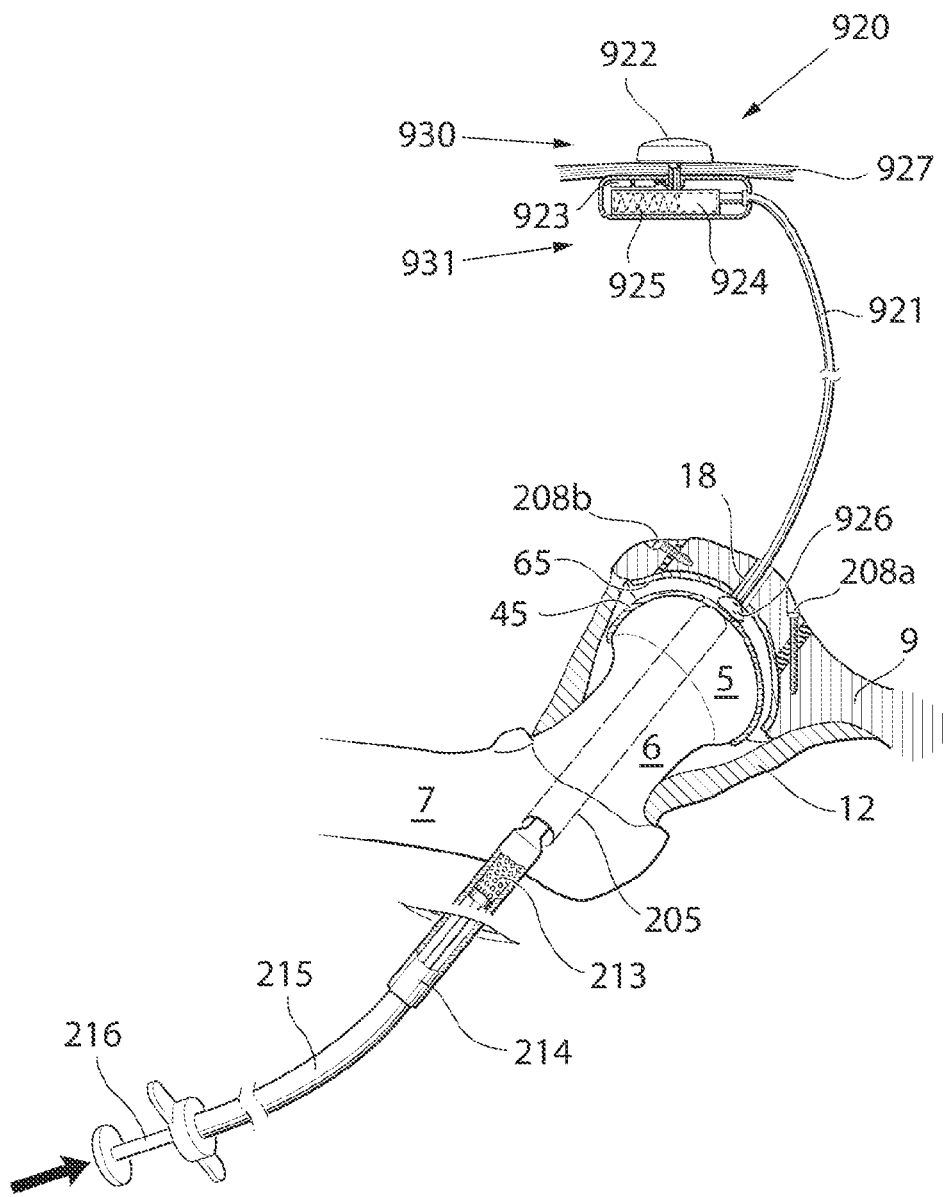

HIP JOINT DEVICE, SYSTEM AND METHOD

This application is the U.S. national phase of International Application No. PCT/SE2010/050811, filed 12 Jul. 2010, which designated the U.S. and claims the benefit of U.S. Provisional Nos.: 61/229,755, filed 30 Jul. 2009; 61/229,738 filed 30 Jul. 2009, 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,735 filed 30 Jul. 2009; and which claims priority to Swedish Application Nos.: 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900962-2 filed 10 Jul. 2009; 0900963-0 filed 10 Jul. 2009; 0900965-5 filed 10 Jul. 2009; 0900966-3 filed 10 Jul. 2009; 0900968-9 filed 10 Jul. 2009; 0900969-7 filed 10 Jul. 2009; 0900970-5 filed 10 Jul. 2009; 0900972-1 filed 10 Jul. 2009; 0900973-9 filed 10 Jul. 2009; 0900974-7 filed 10 Jul. 2009; 0900976-2 filed 10 Jul. 2009 and 0900978-8 filed 10 Jul. 2009, the entire contents of each of which are hereby incorporated by reference.

FIELD OF INVENTION

The present invention relates generally to a medical device for implantation in a human patient.

BACKGROUND

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment of hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is done through a lateral incision in the hip and upper thigh and through, Fascia Lata and the lateral muscles of the thigh. To get access to the joint, the supporting hip joint capsule attached to Femur and Ilium needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The surgery typically requires one week of hospitalization due to the increased risk of infection. The recovery process is on average about 6 weeks, but even after this period the patient should not perform any physical activates that places large strain on the joint.

The correct placement of the prosthesis or prosthetic parts is an important part of the operation since it affects the hip joint's ability to heal correctly, and also affects the function of the hip joint after the hip joint replacement surgery. Due to limited reach and visibility inside the hip joint, the placing of the prosthesis is a difficult and time consuming step of the operation with numerous possibilities for errors.

SUMMARY

An implantable medical device for implantation in a hip joint of a human patient is provided. The hip joint comprises the caput femur shaped like a ball, being connected to the collum femur and being the upper extremity of the femoral bone. The collum femur and caput femur having a longitudinal axial distribution with a longitudinal caput femur centre axis reaching from the collum femur, in the centre of the collum femur and caput femur and towards the acetabulum. The acetabulum is a bowl shaped section of the pelvic bone, with an opening towards the caput femur, the acetabulum have an acetabulum centre axis reaching from the centre of the bottom of the bowl towards the centre of the opening and the caput femur. The caput femur centre axis is identical with the acetabulum centre axis in a special centred position, when the caput femur being aligned, centred and symmetrical in the acetabulum. The caput femur and acetabulum each have a hip joint carrying surface, facing each other and contacting each other, the hip joint carrying surfaces, carrying weight in the hip joint. The medical device comprises: at least one artificial hip joint surface adapted to replace at least the surface of at least one of the caput femur and acetabulum. At least one artificial hip joint surface comprises: a positioning hole with at least one opening in said at least one artificial hip joint surface. The hole is adapted to be placed and dimensioned such that the medical device is adapted to be fitted using a positioning shaft and at least partly surround the shaft, for positioning the at least one artificial hip joint surface in a desired position in the hip joint. The hole is adapted to be fitted using the positioning shaft, when the shaft is stabilized and placed in at least one of the femoral bone and the pelvic bone for positioning said medical device inside the hip joint.

According to one embodiment the medical device comprises an artificial caput femur or an artificial caput femur surface, which could comprise at least two artificial caput femur surface parts adapted to be interconnected to form the artificial caput femur surface during an operation. Each of the at least two artificial caput femur surface parts could comprise a positioning hole adapted to at least partly surround a positioning shaft.

According to one embodiment the collum femur has an axial distribution leading to the caput femur, which has a substantially ball shaped configuration with a maximum diameter substantially perpendicular to the centre axis of the prolongation of the axial distribution of the collum femur. The caput femur is normally placed in an acetabulum creating the hip joint.

According to another embodiment the artificial caput femur surface further comprises at least one first beyond part of the artificial caput femur surface adapted to cover and/or go into the bone of the caput femur on at least a part of the caput femur beyond the maximum diameter of the caput femur, away from the acetabulum cup towards the collum femur, when mounted on the caput femur in its functional position in the joint. The at least one first beyond part is adapted to have a closest perpendicular distance to the centre axis, being smaller than the distance between the periphery of the maximum diameter of the caput femur and the centre axis. The medical device thus is adapted to create a more stable position of said artificial caput femur surface when mounted on the caput femur in the functional position.

The hip joint has a ball shaped caput femur being the proximal part of the femoral bone with a convex hip joint surface and a bowl shaped acetabulum as part of the pelvic bone with a concave hip joint surface. According to one embodiment the artificial caput femur surface comprises an artificial concave hip joint surface adapted to be fixated to the femoral bone.

The implantable medical device could have a largest diameter or a largest cross-sectional distance, and an opening. The largest diameter or cross sectional distance is adapted to be changed during an operation.

According to another embodiment of the implantable medical device, the artificial hip joint surface further comprises an artificial acetabulum or an artificial acetabulum surface. The artificial acetabulum surface could comprises a first positioning hole and a second positioning hole. The artificial acetabulum surface is adapted to be aligned with the artificial caput femur surface in a special position and adapted to use the positioning shaft placed in at least one of the femoral and pelvic bone, placed through at least one of the first positioning hole in the caput femur surface and the second positioning hole in the acetabulum surface and further placed at least partly through at least one of the first positioning hole in the caput femur surface and the second positioning hole in the acetabulum surface.

According to another embodiment the artificial acetabulum surface and the artificial caput femur surface are adapted to be in moveable connection with each other when implanted in the hip joint.

According to one embodiment the implantable medical device is adapted to be fixated to at least one of the caput femur, the collum femur and the femoral bone using a fixation element, which could be a fixation element selected from a group consisting of; at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, and other mechanical connecting members.

According to another embodiment the artificial hip joint surface comprises an artificial acetabulum or an artificial acetabulum surface, which could comprises at least two artificial acetabulum surface parts adapted to be interconnected to form the artificial acetabulum surface during an operation. Each of the at least two artificial acetabulum surface parts could comprise a positioning hole adapted to at least partly surround a positioning shaft.

The hip joint has a ball shaped caput femur, being the proximal part of the femoral bone, with a convex hip joint surface, and a bowl shaped acetabulum as part of the pelvic bone with a concave hip joint surface. The artificial acetabulum surface, according to one embodiment, could comprise an artificial convex hip joint surface adapted to be fixated to the pelvic bone.

The artificial acetabulum surface has a largest diameter or a largest cross-sectional distance, and an opening. According to one embodiment the largest diameter or cross sectional distance could be adapted to be changed during an operation.

The positioning hole according to any of the embodiments herein could be substantially circular, non-circular or have a cut circumference.

The implantable medical device according to any of the embodiments could be adapted to inserted through the hip joint capsule or the pelvic bone and could be mounted onto said positioning shaft inside of the hip joint.

According to one embodiment the at least two artificial caput femur surface parts could comprise a positioning hole adapted to at least partly surround a positioning shaft.

According to one embodiment each of the at least two artificial acetabulum surface parts could comprise a positioning hole adapted to at least partly surround a positioning shaft.

The artificial acetabulum surface could be adapted to be fixated to the pelvic bone using a fixation element, such as a fixation element selected from a group consisting of; at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, and other mechanical connecting members.

A positioning shaft adapted to position a medical device inside of the hip joint of a human patient is further provided. The positioning shaft could be elongated and further adapted to be introduced into at least one of the femoral bone and the pelvic bone during positioning of a medical device inside the hip joint.

According to one embodiment the positioning shaft is adapted to be fixated to the at least one of the femoral bone and the pelvic bone during positioning of the medical device inside the hip joint.

The artificial hip joint surface comprises an artificial acetabulum or an artificial acetabulum surface. The hole, when fitted with the positioning shaft, could be adapted to centre and hold the artificial acetabulum or an artificial acetabulum surface during fixation thereof in the hip joint.

The artificial hip joint surface could comprise an artificial caput femur or an artificial caput femur surface. The hole, when fitted with the positioning shaft, could be adapted to centre and hold the artificial caput femur or an artificial caput femur surface during fixation thereof in the hip joint.

The artificial hip joint surface could further comprise an artificial acetabulum or an artificial acetabulum surface. The hole, when fitted with the positioning shaft, could be adapted to centre and hold both the artificial caput femur or an artificial caput femur and the artificial acetabulum or an artificial acetabulum surface during fixation thereof in the hip joint.

The artificial caput femur surface could according to one embodiment comprise a convex shape towards the centre of the hip joint, and the artificial acetabulum surface could comprise a concave shape towards the centre of the hip joint. The artificial convex caput femur surface could be adapted to be fixated to the pelvic bone of the human patient, and the artificial concave acetabulum surface could be adapted to be fixated to the femoral bone of the human patient.

The caput femur has a convex hip joint surface towards the centre of the hip joint and the acetabulum has a concave hip joint surface towards the centre of the hip joint. At least one artificial hip joint surface comprises an artificial caput femur or an artificial caput femur surface, having a convex shape towards the centre of the hip joint, comprising a first hole, and an artificial acetabulum or an artificial acetabulum surface, having a concave form towards the centre of the hip joint, comprising a second hole. The artificial caput femur or the artificial caput femur surface and the artificial acetabulum or the artificial acetabulum surface are adapted to be centered in the hip joint by the positioning shaft placed in said hole and at least one of the femoral or pelvic bone. The artificial convex caput femur or artificial convex caput femur surface has the first hole placed in the convex part, for enabling the positioning shaft to be introduced into said hole and centering said artificial convex caput femur or said artificial convex caput femur surface, when placed in the hip joint. Furthermore the artificial concave acetabulum or the artificial concave acetabulum surface has the second hole placed in the concave part, for enabling the positioning shaft to be introduced into the hole and centering the artificial concave acetabulum or the artificial concave acetabulum surface, when placed in the hip joint.

The artificial concave acetabulum or the artificial concave acetabulum surface could according to one embodiment have the second hole placed in the centre of the concave part. The artificial convex caput femur or artificial convex caput femur surface could have the first hole placed in the centre of said convex part, adapted for enabling the positioning shaft to be introduced into said hole and centering said artificial convex caput femur or said artificial convex caput femur surface and said artificial concave acetabulum or said artificial concave acetabulum surface, when placed in the hip joint, and when said hip joint is placed in said special centered position.

The artificial convex caput femur surface could be adapted to be fixated to the pelvic bone of the human patient, and the artificial concave acetabulum surface could be adapted to be fixated to the femoral bone of the human patient.

According to another embodiment the positioning shaft further comprises a screw thread adapted to fixate the positioning shaft to at least one of: the femoral bone and the pelvic bone, during positioning of the medical device inside the hip joint. The positioning shaft could be adapted to be removed from the connection with at least one of the femoral bone and the pelvic bone, after the positioning of the medical device inside the hip joint.

According to one embodiment the positioning shaft is adapted to have a first and second state. The first state is a state in which the positioning shaft is flexible, and the second state is a state in which the positioning shaft is adapted to be less flexible than in the first state.

The positioning shaft could be adapted to position the medical device in at least one axis, in at least two axis, in at least three axis and/or in at least one plane.

According to one embodiment the positioning shaft is adapted to be placed in a positioning hole of the medical device.

The positioning shaft could be adapted to position a medical device comprising at least two medical device parts, and the positioning shaft could be adapted to be placed in a positioning hole in at least one of the at least two medical device parts.

According to one embodiment the positioning shaft has an area, substantially perpendicular to its elongated distribution, adapted to be positioned in said positioning hole, being substantially circular or non-circular.

The positioning shaft is adapted to be positioned in a positioning hole, which could have a cut circumference.

The positioning shaft could be adapted to receive a medical device inserted into the hip joint through the hip joint capsule or through the pelvic bone.

The positioning shaft, according to one embodiment could be adapted to receive a medical device to be mounted onto the positioning shaft inside of the hip joint.

A medical device system comprising a first medical device, according to any of the embodiments herein, and a second medical device, being a medical according to any of the embodiments herein, and a positioning shaft according to any of the embodiments herein.

According to one embodiment of the medical device system, the first and second medical devices are adapted to be mounted onto the positioning shaft inside of the hip joint.

According to yet another embodiment of the medical device system, the first and said second medical device are adapted to be mounted onto the positioning shaft outside of the hip joint.

According to yet another embodiment the medical device system, further comprises an implantable lubrication system, the implantable lubrication system is adapted to lubricate the first and second medical devices after the first and second medical device has been positioned in the hip joint.

A medical device system for use in a hip joint of a patient is further provided. The system comprises a first positioning shaft according to any of the embodiments above, and a second positioning shaft according to any of the embodiments above. The first positioning shaft is adapted to position a first part of a medical device in the hip joint, and the second positioning shaft is adapted to position a second part of the medical device in the hip joint.

According to another embodiment of the medical device system, the first part of the medical device and the second part of the medical device are adapted to be connected to each other after implantation in the hip joint of the patient.

According to yet another embodiment of the medical device system the first positioning shaft and the second positioning shaft are adapted to be connected to each other after implantation in the hip joint of the patient.

The medical device according to any of the embodiments herein could comprise an artificial acetabulum or an artificial acetabulum surface, and the hole, when fitted with the positioning shaft, could be adapted to centre and hold the artificial acetabulum or an artificial acetabulum surface during fixation thereof in the hip joint.

According to another embodiment of the medical device, the artificial hip joint surface comprises an artificial caput femur or an artificial caput femur surface. The hole, when fitted with the positioning shaft, could be adapted to centre and hold the artificial caput femur or an artificial caput femur surface during fixation thereof in the hip joint.

The artificial hip joint surface could further comprise an artificial acetabulum or an artificial acetabulum surface. The hole, when fitted with the positioning shaft, could be adapted to centre and hold both the artificial caput femur or an artificial caput femur and the artificial acetabulum or an artificial acetabulum surface, during fixation thereof in the hip joint.

According to one embodiment the artificial caput femur surface comprises a convex shape towards the centre of the hip joint, and the artificial acetabulum surface comprises a concave shape towards the centre of the hip joint. The artificial convex caput femur surface could be adapted to be fixated to the pelvic bone of the human patient, and the artificial concave acetabulum surface could be adapted to be fixated to the femoral bone of the human patient.

According to one embodiment the medical device could comprise a positioning shaft adapted to be placed in the hole, for centering the artificial hip joint surface, when placed in the hip joint. The at least one artificial hip joint surface could comprise an artificial acetabulum or an artificial acetabulum surface, the positioning shaft, when fitted in said hole, could be adapted to center and hold the artificial acetabulum or the artificial acetabulum surface during fixation thereof in the hip joint.

The medical according to any of the embodiments above could comprise a positioning shaft adapted to be placed in the hole for centering the artificial hip joint surface, when placed in the hip joint. At least one artificial hip joint surface could comprise an artificial caput femur or an artificial caput femur surface, and the positioning shaft, when fitted in the hole, is adapted to centre and hold the artificial caput femur or an artificial caput femur surface during fixation thereof in the hip joint.

According to one embodiment the medical device, according to any of the embodiments above, comprises a positioning shaft adapted to be placed in the hole for centering the at least one artificial hip joint surface, when placed in the hip joint. The artificial hip joint surface further comprises an artificial acetabulum or an artificial acetabulum surface, the positioning shaft, when fitted in the hole, could be adapted to centre and hold both the artificial caput femur or the artificial caput femur surface, and the artificial acetabulum, or an artificial acetabulum surface, during fixation thereof in the hip joint.

According to one embodiment the artificial caput femur surface comprises a convex shape towards the centre of the hip joint, and the artificial acetabulum surface comprises a concave shape towards the centre of the hip joint. The artificial convex caput femur surface could be adapted to be fixated to the pelvic bone of the human patient, and the artificial concave acetabulum surface could be adapted to be fixated to the femoral bone of the human patient.

According to another embodiment of the medical device, the caput femur have a convex hip joint surface towards the centre of the hip joint, and the acetabulum have a concave hip joint surface towards the centre of the hip joint, and at least one artificial hip joint surface comprises: an artificial caput femur or an artificial caput femur surface, having a convex shape towards the centre of the hip joint, comprising a first hole, and an artificial acetabulum or an artificial acetabulum surface, having a concave form towards the centre of the hip joint, comprising a second hole. The artificial caput femur or the artificial caput femur surface and the artificial acetabulum or the artificial acetabulum surface are adapted to be centred in the hip joint by the positioning shaft placed in the hole and at least one of the femoral or pelvic bone. The artificial convex caput femur or the artificial convex caput femur surface have the first hole placed in the centre of the convex part, for enabling the positioning shaft to be introduced into the hole and centering the artificial convex caput femur or the artificial convex caput femur surface, when placed in the hip joint, and the artificial concave acetabulum or the artificial concave acetabulum surface have the second hole placed in the centre of the concave part, for enabling the positioning shaft to be introduced into the hole and centering the artificial concave acetabulum or the artificial concave acetabulum surface, when placed in the hip joint.

According to one embodiment the artificial convex caput femur surface is adapted to be fixated to the pelvic bone of the human patient, and the artificial concave acetabulum surface is adapted to be fixated to the femoral bone of the human patient.

The caput femur has a convex hip joint surface towards the centre of the hip joint, and the acetabulum, has a concave hip joint surface towards the centre of the hip joint. According to one embodiment the medical device further comprises a positioning shaft adapted to centre the artificial hip joint surface when placed in the hole, wherein the at least one artificial hip joint surface comprises; an artificial caput femur or an artificial caput femur surface, having a convex form towards the centre of the hip joint, comprising a first hole. The artificial hip joint surface further comprises an artificial acetabulum or an artificial acetabulum surface, having a concave form towards the centre of the hip joint, comprising a second hole. The artificial caput femur or the artificial caput femur surface and the artificial acetabulum or the artificial acetabulum surface are adapted to be centred in the hip joint by the positioning shaft placed in the hole and in at least one of: the femoral bone and the pelvic bone. The artificial convex caput femur or the artificial convex caput femur surface having the first hole placed in the centre of the convex part, for enabling the positioning shaft to be introduced into the hole and centreing the artificial convex caput femur or the artificial convex caput femur surface, when placed in the hip joint, and the artificial concave acetabulum or the artificial concave acetabulum surface having the second hole placed in the centre of the concave part, for enabling the positioning shaft to be introduced into the hole and centreing the artificial concave acetabulum or the artificial concave acetabulum surface, when placed in the hip joint.

In one embodiment the artificial convex caput femur surface is adapted to be fixated to the pelvic bone of the human patient, and the artificial concave acetabulum surface is adapted to be fixated to the femoral bone of the human patient.

According to another embodiment the positioning shaft is adapted to receive the hip joint surfaces inserted into the hip joint through the hip joint capsule and/or the pelvic bone. However it is equally conceivable that the positioning shaft is adapted to receive the hip joint surfaces to be mounted onto said positioning shaft, inside of the hip joint.

Method

A method of treating a hip joint of a patient is further provided. The method comprising the steps of: cutting the skin of the patient, dissecting an area of the hip joint, placing a positioning shaft in the hip joint, providing a medical device comprising a positioning hole, said hole being adapted to be placed and dimensioned such that the medical device is adapted to be fitted using said positioning shaft, placing said medical device at least partly surrounding said positioning shaft, fixating said medical device comprising an artificial hip joint surface in the right position in the hip joint using said positioning shaft.

The method could further comprise the step of removing said positioning shaft.

The step of fixating the medical device in the hip joint could according to one embodiment comprise the step of fixating the medical device in the hip joint using a fixation element selected from a group consisting of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, and other mechanical connecting members.

The step of fixating the medical device in the hip joint could comprise the step of fixating the medical device to the caput femur or femoral bone.

The step of fixating the medical device in the hip joint could comprise the step of fixating the medical device to the acetabulum or pelvic bone.

The step of placing a positioning shaft in the hip joint could comprise the step of placing a positioning shaft in the caput femur or femoral bone.

The step of placing a positioning shaft in the hip joint could comprise the step of placing a positioning shaft in the acetabulum or pelvic bone.

The step of placing the medical device at least partly surrounding said positioning shaft, could comprise the step of placing an artificial acetabulum or artificial acetabulum surface onto the positioning shaft in the hip joint, wherein said positioning shaft is introduced into said hole.

The method according to any of the embodiment herein could comprise the step of placing said medical device at least partly surrounding the positioning shaft, which could comprise placing an artificial caput femur or artificial caput femur surface onto the positioning shaft in the hip joint, the positioning shaft could be introduced into the hole.

The step of placing the medical device at least partly surrounding the positioning shaft could comprise placing an artificial acetabulum or artificial acetabulum surface onto the positioning shaft in the hip joint, wherein the positioning shaft is introduced into said hole.

The at least one of the artificial caput femur or artificial caput femur surface and the artificial acetabulum or artificial acetabulum have a through going hole with an inlet and an outlet. The method could further comprise introducing the positioning shaft into said hole inlet and passing out from the hole outlet.

An arthroscopic method of treating a hip joint of a patient is further provided. The method comprises the steps of: inserting at least one needle or a tube like instrument into the patient's hip joint, using the needle or tube like instrument to fill the joint with a fluid, placing at least two arthroscopic trocars in the joint, inserting a camera through one of the arthroscopic trocars into the joint, dissecting an area of the hip joint, placing a positioning shaft in the hip joint, providing a medical device comprising a positioning hole, said hole being adapted to be placed and dimensioned such that the medical device is adapted to be fitted using said positioning shaft, placing said medical device at least partly surrounding said positioning shaft, fixating said medical device in the right position in the hip joint using said positioning shaft.

The method could further comprise the step of removing said positioning shaft.

The step of fixating the medical device in the hip joint could according to one embodiment comprise the step of fixating the medical device in the hip joint using a fixation element selected from a group consisting of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, and other mechanical connecting members.

The step of fixating the medical device in the hip joint could comprise the step of fixating the medical device to the caput femur or femoral bone.

The step of fixating the medical device in the hip joint could comprise the step of fixating the medical device to the acetabulum or pelvic bone.

The step of placing a positioning shaft in the hip joint could comprise the step of placing a positioning shaft in the caput femur or femoral bone.

The step of placing a positioning shaft in the hip joint could comprise the step of placing a positioning shaft in the acetabulum or pelvic bone.

The step of placing the medical device at least partly surrounding said positioning shaft, could comprise the step of placing an artificial acetabulum or artificial acetabulum surface onto the positioning shaft in the hip joint, wherein said positioning shaft is introduced into said hole.

The method according to any of the embodiment herein could comprise the step of placing said medical device at least partly surrounding the positioning shaft, which could comprise placing an artificial caput femur or artificial caput femur surface onto the positioning shaft in the hip joint, the positioning shaft could be introduced into the hole.

The step of placing the medical device at least partly surrounding the positioning shaft could comprise placing an artificial acetabulum or artificial acetabulum surface onto the positioning shaft in the hip joint, wherein the positioning shaft is introduced into said hole.

The at least one of the artificial caput femur or artificial caput femur surface and the artificial acetabulum or artificial acetabulum have a through going hole with an inlet and an outlet. The method could further comprise introducing the positioning shaft into said hole inlet and passing out from the hole outlet.

Please note that any embodiment or part of embodiment, feature, method, associated system, part of system described herein may be combined in any way. Please note that the description in general should be seen as describing both of an apparatus and a method.

BRIEF DESCRIPTION OF DRAWINGS

The invention is now described, by way of example, with reference to the accompanying drawings, in which:

FIG. 9 shows the process of placing an artificial caput femur surface onto the caput femur, through a hole in the pelvic bone, FIG. 10 shows the process of placing an artificial caput femur surface onto the caput femur, through a hole in the pelvic bone, FIG. 11 shows the removal of the positioning shaft, FIG. 12 shows the placing of an artificial caput femur surface onto the caput femur, FIG. 13 shows the placing of an artificial caput femur surface onto the caput femur, FIG. 14 shows the removal of the positioning shaft, FIG. 15 shows the placing of adhesive on a section of a surface of the collum femur, FIG. 16 shows the placing of a medical device inside the hip joint through a hole in the pelvic bone, FIG. 17 shows the hip joint in section when a medical device is being fixated, FIG. 18 shows the placing of a prosthetic part in the hole of the pelvic bone, FIG. 29 shows the hip joint in section when a concave surface id created in the collum femur and caput femur, FIG. 30 shows the injecting of an adhesive in the concave surface in the caput femur and collum femur, FIG. 31 shows the positioning of a medical device in the collum femur and caput femur through a hole in the pelvic bone, FIG. 37 shows an embodiment of a medical device, FIGS. 38a-e shows a medical device in an operable embodiment, FIG. 39a shows a medical device in an expandable embodiment, in a first state, FIG. 39b shows a medical device in an expandable embodiment, in a second state, FIG. 41 shows an artificial acetabulum surface according to one embodiment, FIG. 42a shows the femoral bone when a medical device is being placed on the caput femur, FIG. 42b shows the femoral bone when a medical device is being placed on the caput femur, in a top view, FIG. 43a,b shows an instrument for placing positioning shafts in the caput femur and collum femur, FIG. 44a shows the placing of a prosthetic part in the hole in the pelvic bone, FIG. 44b shows the operation of the prosthetic part in the hole in the pelvic bone, FIG. 45 shows hip joint in section when a prosthetic part is being placed, FIG. 46 shows the hip joint in section when a bone plug or medical device is being fixated, FIG. 51 shows an implantable lubricating system.

DETAILED DESCRIPTION

Figure 1A:
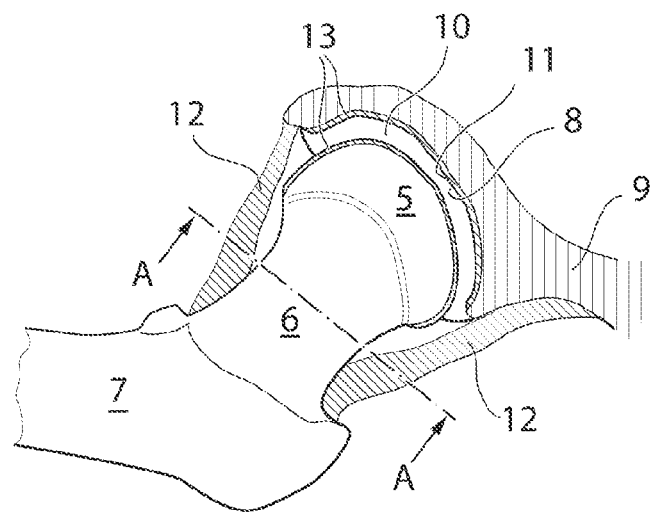
FIG. 1a shows the hip joint in section.

Biocompatible material is to be understood as being a material with low level of immune response. Biocompatible materials are sometimes also referred to as biomaterials. Analogous is biocompatible metals a biocompatible metal with low immune response such as titanium or tantalum. The biocompatible metal could also be a biocompatible alloy comprising at least one biocompatible metal.

A metal alloy is to be understood as a mixture of two or more elements in solid solution in which the major component is a metal. A steel alloy is hence an alloy wherein one of the components is steel which in turn is an alloy of iron and carbon. A titanium alloy is hence an alloy wherein one of the components is titanium.

Elasticity is to be understood as a materials ability to deform in an elastic way.

Carrying surface and weight carrying surface is to be understood as a surface adapted to carry weight inside of the hip joint.

Form fitting is to be understood as an element having a part or section which is adapted to enable a mechanical connection of said element to at least one other element using said part or section. Form fitted structure is a structure of an element which enables form fitting.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with artificial surfaces somewhat different than the functional hip movements of a natural hip joint.

The functional position of an implantable medical device or prosthesis is the position in which the hip joint can perform functional hip movements.

Functional hip joint is a hip joint that can perform functional hip movements either with or without an implanted medical device or prosthesis.

Connection line is to be understood as a line of the connecting surface of at least two medical device parts connecting to each other.

In the following a detailed description of preferred embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE and UHMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

FIG. 1a shows the hip joint of a human patient in section. The hip joint comprises a caput femur 5 placed at the very top of collum femur 6 which is the top part of the femur bone 7.

The caput femur 5 is in connection with the acetabulum 8 which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12, the patient can fully recover and place equal amount of strain on an artificial joint as is possible on a natural one.

Figure 1B:
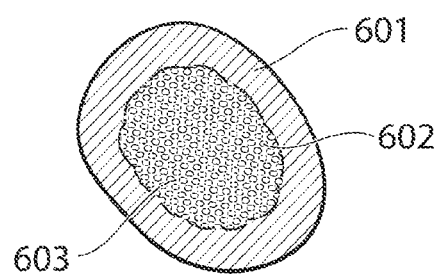
FIG. 1b shows the collum femur in section having cancellous bone and cortical bone.

FIG. 1b shows the collum femur 6 in section. Both caput femur 5 and collum femur 6 further comprises cortical bone 601, the outer more sclerotic bone, and cancellous bone 602, placed in the bone marrow 603. The cortical bone is much more dense and beneficial to anchor a prosthesis two, or to place a positioning shaft in, whereas the cancellous bone 602 provides stability in the bone due to its sandwich construction, but is easy to remove to make room for a fixation member of a prosthesis.

Figure 2:
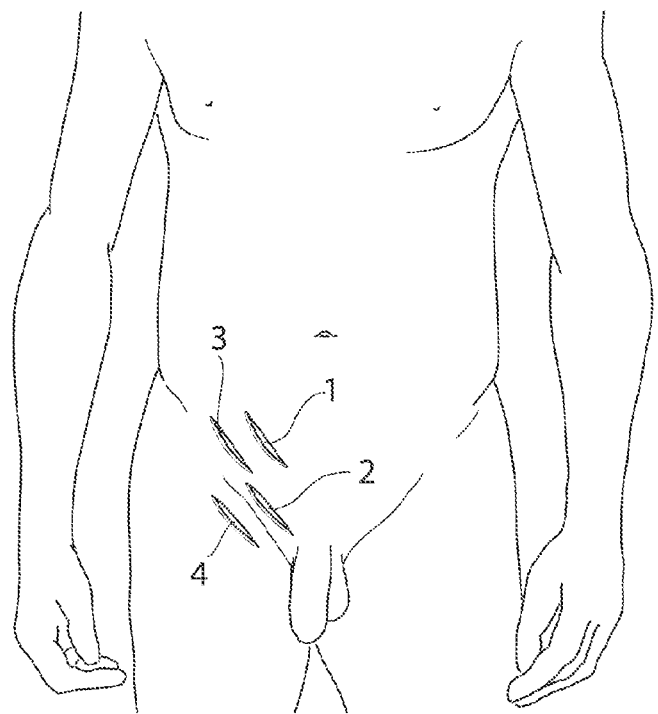
FIG. 2 shows the human patient in a frontal view when incisions are being made in the abdominal region.

FIG. 2 shows a frontal view of the body of a human patient. A surgical method of operating the hip joint from the opposite side from acetabulum, is according to a first embodiment performed starting with an incision 1 in the abdominal wall of the human patient. The incision 1 passes through the abdominal muscles in to the abdomen of the human patent. In a second embodiment the incision 2 is conducted through the abdominal muscles and in to the pelvic area, below peritoneum. According to a third embodiment the incision 3 is performed just between Illium and the surrounding tissue, an incision 3 which could enable the pelvic bone to be dissected with very little penetration of fascia and muscular tissue. According to a fourth embodiment the incision 4 is made in the inguinal channel. In all of the four embodiments the tissue surrounding the pelvic bone 9 in the area opposite to acetabulum is removed or penetrated which enables the surgeon to reach the pelvic bone 9.

Figure 3:
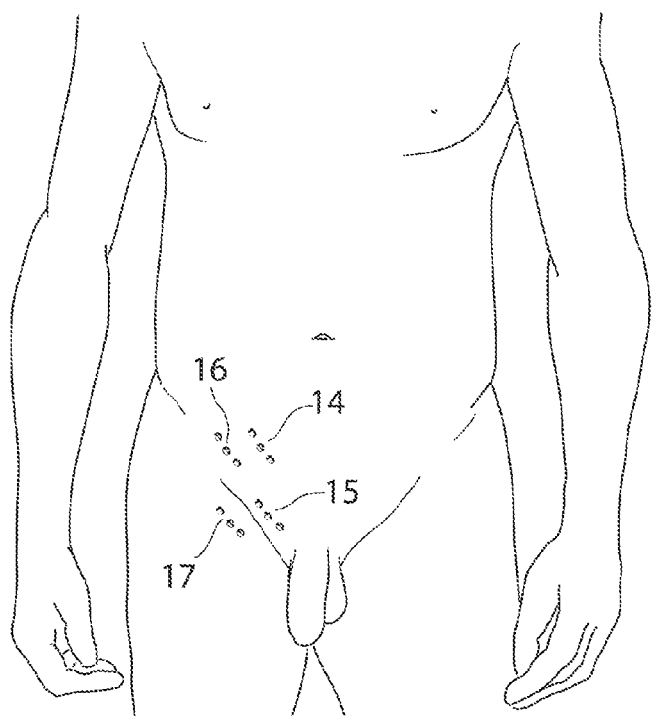
FIG. 3 shows the human patient in a frontal view when incisions are being made in the abdominal region.

FIG. 3 shows a frontal view of the body of a human patient. A laparoscopic/arthroscopic method of operating the hip joint, from the opposite side from acetabulum, is according to a first embodiment performed starting with making small incisions 14 in the abdominal wall of the human patient. The small incisions enable the surgeon to insert laparoscopic trocars into the abdomen of the human patient. According to the first embodiment the incisions 14 passes through the abdominal wall, in to the abdomen of the human patent. According to a second embodiment the small incisions 15 is conducted through the abdominal wall, in to the pelvic area, below peritoneum. According to a third embodiment the small incisions 16 is performed just between Illium and the surrounding tissue, an incision 16 which could enable the pelvic bone to be dissected with very little penetration of fascia and muscular tissue. According to a fourth embodiment the incision 17 is made in the inguinal channel. In all of the four embodiments the tissue surrounding the pelvic bone 9 in the area opposite to acetabulum 8 is removed or penetrated which enables the surgeon to reach the pelvic bone 9.

Figure 4:
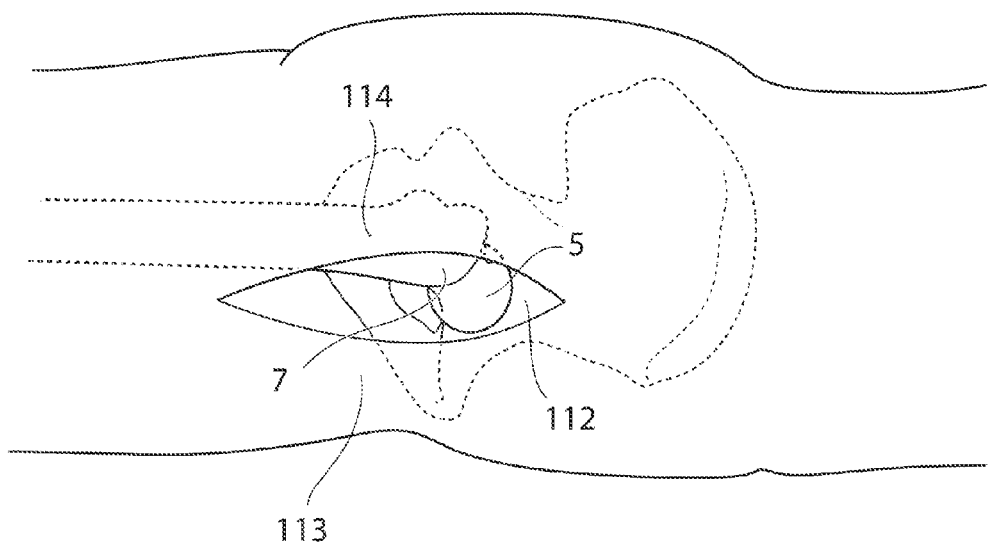
FIG. 4 shows a lateral view of a human patient.

FIG. 4 shows a lateral view of a conventional hip joint surgery where an incision 112 is made in the thigh 113 enabling the surgeon to reach the femur bone 7 on which the caput femur 5 is located. In a conventional hip joint surgery the hip joint is accessed through the hip joint capsule, which forces the surgeon to, at least partly, savage the structure of the capsule.

Figure 5:
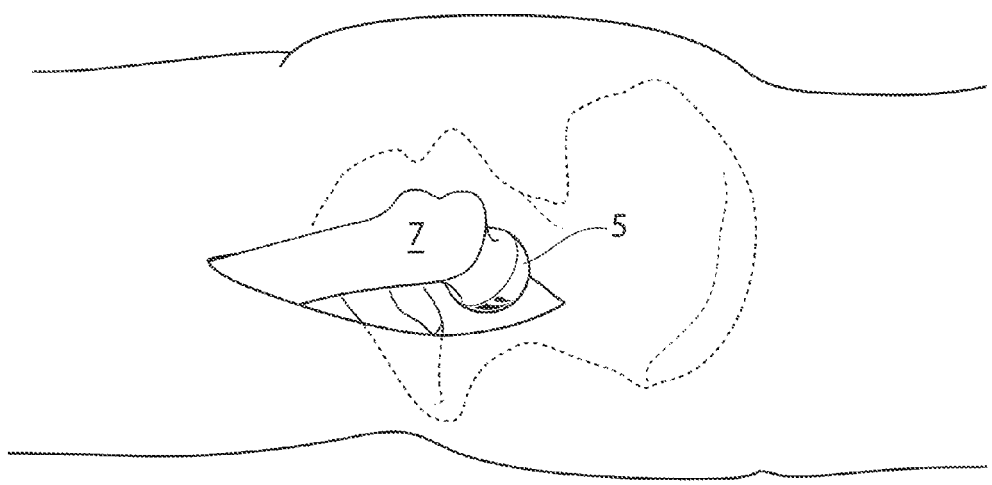
FIG. 5 shows a lateral view of a human patient when the femoral bone dissected.

FIG. 5 to enable the surgeon to reach the caput femur 5 the femoral bone 7 comprising the caput femur 5 is placed outside of the hip joint capsule 12. The surgeon can thereby perform surgical modifications on the caput femur including fixating holding members or prosthetic parts to the surface or the bone structure of any part of the femoral bone 7.

Figure 6:
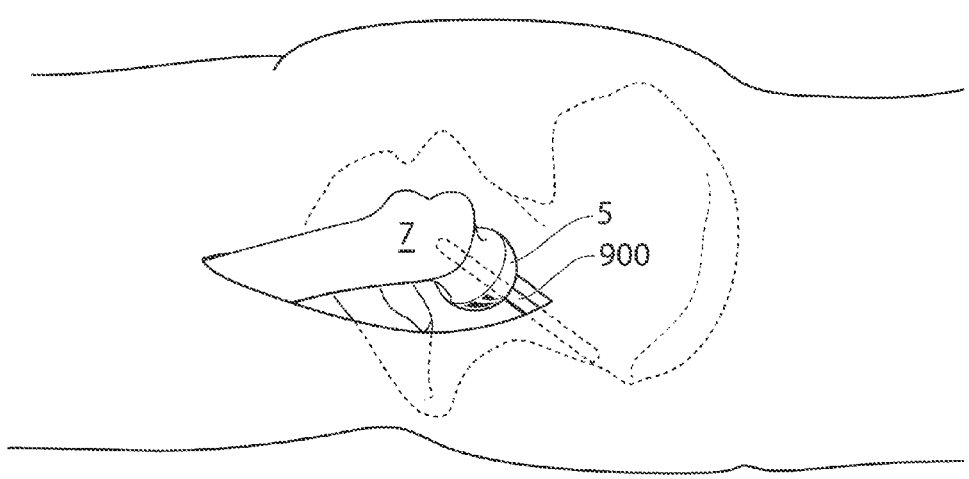
FIG. 6 shows a lateral view of the human patient when a positioning shaft is being placed in the caput and collum femur.

FIG. 6 shows the placing of a positioning shaft 900 in the caput femur 5 and collum femur 6, penetrating the surface and the cortical bone of the caput femur 5. For example the positioning shaft can be fixated to the bone structure of the femoral bone 7 the collum femur 6 or the caput femur 5 using mechanical fixating members, adhesive, a threaded section of the positioning shaft 900 or using an expanding part or section of the positioning shaft 900.

Figure 7:
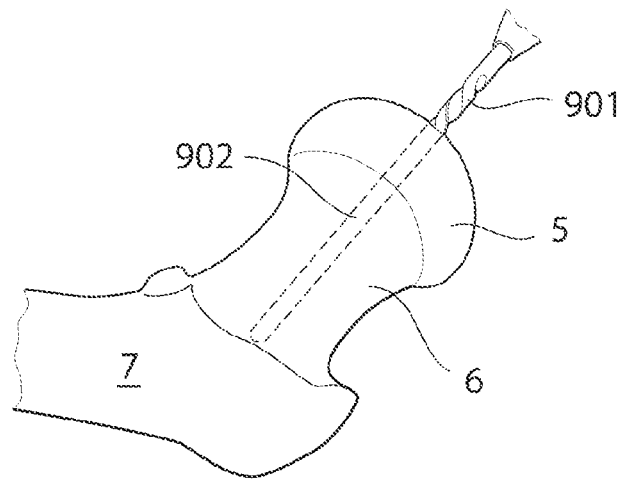
FIG. 7 shows the step of creating a hole in the caput and collum femur.

FIG. 7 shows the femoral bone 7, comprising the collum femur 6 and the caput femur 5, when a hole 902 going through the surface and the cortical bone of the caput femur 5 and in to the cancellous bone of the caput femur 5 and collum femur 6. The hole 902 is created using a drill 901, which could be powered using an operation device or through manual force.

Figure 8A:
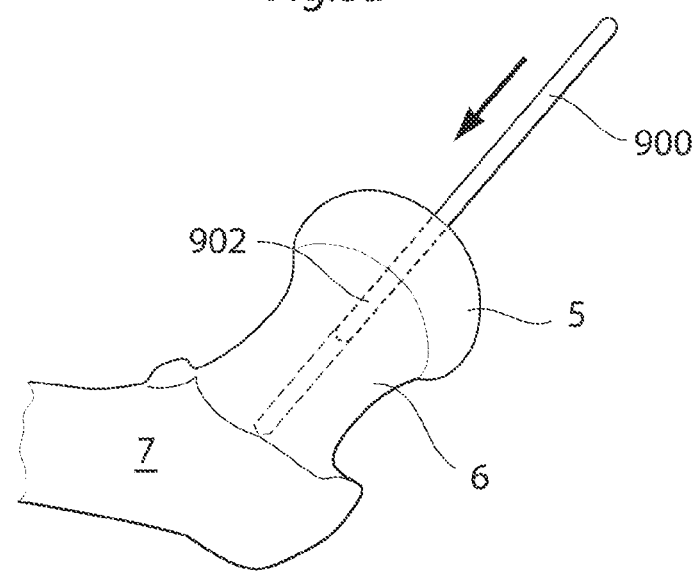
FIG. 8a shows the placing of a positioning shaft in the caput femur and collum femur.

FIG. 8a shows the placing of a positioning shaft 900 in the hole 902 in the surface of the caput femur 5 the cortical bone of the caput femur 5 and the cancellous bone of the collum femur 6. For example the positioning shaft 900 can be fixated to the bone structure of the femoral bone 7 the collum femur 6 or the caput femur 5 using mechanical fixating members, adhesive, a threaded section of the positioning shaft 900 or using an expanding part or section of the positioning shaft 900.

Figure 8B:
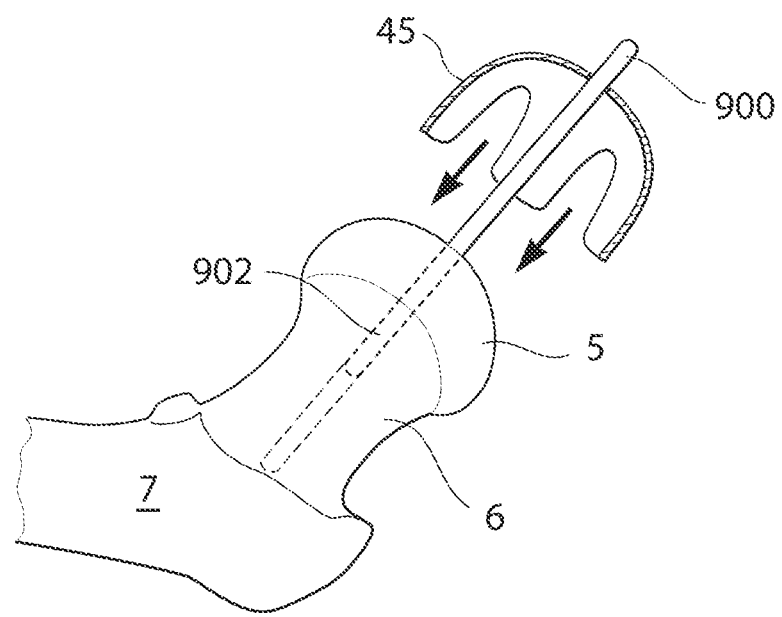
FIG. 8b shows the placing of a medical device onto the caput femur using the positioning shaft.

FIG. 8b shows the step of placing an artificial caput femur surface 45 on the caput femur 5 using the positioning shaft 900. The artificial caput femur surface 45 comprises a hole adapted to encircle the positioning shaft 900 such that the positioning shaft 900 positions and centers the artificial caput femur surface 45 in a suitable position on the caput femur 5.

FIG. 9 shows the hip joint in section, when an artificial caput femur surface 45 is positioned on the caput femur using a positioning shaft 900 placed in a hole 902 in the caput femur 5 and collum femur 6. The caput femur 5 is according to this embodiment inserted through a hole 18 in the pelvic bone 9 from the opposite side from acetabulum 8, which also is the way the positioning shaft 900 has been inserted in the caput femur 5 and collum femur 6. To enable the artificial caput femur to be inserted through a hole 18 in the pelvic bone 9 having a diameter d1 smaller than the diameter d2 required for the artificial caput femur surface 45 to reach over the caput femur 5. The artificial caput femur surface 45 therefore comprises elastic material which enables the artificial caput femur surface 45 to in a first state have a first diameter d1, for passing through the hole 18 in the pelvic bone 9, and in a second state have a second diameter d2 for reaching over the caput femur 5, and in a third state have a third diameter d3 for clasping the caput femur 5, thereby creating a stable position inside the hip joint. The artificial caput femur surface comprises a hole adapted to encircle the positioning shaft 900 for positioning and centering the artificial caput femur surface 45 inside the hip joint.

FIG. 10 shows the step of inserting an artificial acetabulum surface 65 through the hole 18 in the pelvic bone 9 using a positioning shaft 900 placed in a hole 902 in the caput femur 5 and the collum femur 6. The positioning shaft 900 assists in the positioning and centering of the artificial caput femur surface 45 to the caput femur 5 in the hip joint. To enable the insertion of the artificial caput femur surface 45 through a hole 18 in the pelvic bone 9 the size of the artificial caput femur surface 45 is adapted to be changed. In a first state for inserting the artificial caput femur surface 45 through a hole 18 in the pelvic bone 9 the artificial caput femur surface 45 has a largest diameter d1, smaller than the diameter of the hole 18 in the pelvic bone 9.

FIG. 11 shows the removal of the positioning shaft 900 from the hole 902 in the caput femur 5, after the placing of the artificial acetabulum surface 65. After the artificial acetabulum surface 65 has passed through the hole 18 in the pelvic bone 9 the surface is expanded to represent the entire contacting surface of the acetabulum 8, and the largest diameter is now d2 which confines the artificial acetabulum surface inside of the hip joint. The use of the positioning shaft 900 also ensures the correct centering of the caput femur surface 45 in relation to the artificial acetabulum surface 65 inside of the hip joint.

FIGS. 12-14 shows the process of placing an artificial caput femur surface 45 on the caput femur 5 in the hip joint through a hole 18 in the pelvic bone 9. The artificial caput femur surface 45 is inserted through the hole 18 in the pelvic bone 9 in its folded state, as shown in FIG. 12, positioned, guided and centered by the positioning shaft 900 fixated to the caput femur 5 and the collum femur 45. After the passing of the hole 18 in the pelvic bone 9 the artificial caput femur surface 45 is expanded as shown in FIG. 13 and eventually clasps the caput femur 5 as shown in FIG. 14, whereafter the positioning shaft 900 is removed, as shown in FIG. 14.

An alternative embodiment of fixation of a medical device comprising an artificial caput femur will now be described with reference to FIGS. 15-18.

FIG. 15 shows the hip joint in section in a step in which the caput femur 5 has been removed and a surface of the section 610 in the collum femur 6 is being prepared for the fixation of an artificial caput femur 600. An injecting member 613 applies and adhesive 614 to the surface of the section 610 of the collum femur 6. The injecting member 613 is adapted to be introduced through a hole 18 in the pelvic bone 9 and to apply the adhesive 614 which was contained within the injecting member 613. Furthermore a positioning shaft 900 is placed in the collum femur 6 from the hole 18 in the pelvic bone 9. The positioning shaft is preferably fixated to the cortical bone of the femoral bone 7 as well as the cancellous bone of the collum femur 6.

FIG. 16 shows the step of introducing and fixating the medical device 600 to the collum femur 6, through a hole 18 in the pelvic bone 9. The stabilizing member 612 is adapted to stabilize the medical device 600 from the outside of the collum femur 6 substantially perpendicular to the longitudinal extension of the collum femur 6, and from the acetabulum side, substantially in line with the longitudinal extension of the collum femur 6 through the stabilizing member 612 being placed in contact with the outside of the collum femur 6 and the surface of the section 610 in the collum femur 6. The stabilizing member 612 is fixated to the outside of the collum femur 6 and/or to the surface of the section 610 in the collum femur 6 by means of the adhesive 614. However the adhesive 614 could be replaced or assisted by bone cement or a mechanical fixation element 615. The medical device 600 is positioned, guided and centered a positioning shaft 900 placed in the collum femur 6 from the hole 18 in the pelvic bone 9. The positioning shaft 900 is preferably fixated to the cortical bone of the femoral bone 7 as well as the cancellous bone of the collum femur 6.

FIG. 17 shows the hip joint in section when the medical device 600 is positioned on the collum femur 6. The stabilizing member 612 is here fixated to the collum femur 6 by means of adhesive 614 and a mechanical fixation element 615, such as a screw or pin.

FIG. 18 shows the hip joint in section when the medical device 600 is positioned on the collum femur 6. The stabilizing member 612 is here fixated to the collum femur by means of adhesive 614. A prosthetic part 98 comprising an artificial acetabulum surface 618 has been positioned in the hole 18 in the pelvic bone 9. The artificial acetabulum surface 618 is adapted to be in direct of indirect connection with the artificial caput femur surface 607. In embodiments where the artificial acetabulum surface 618 is adapted to be in indirect connection with the artificial caput femur surface 607 a lubricating fluid or a lubricating material (not shown) can be placed between said artificial acetabulum surface 618 and said artificial caput femur surface 607. The prosthetic part 98 is adapted to carry the load placed on the artificial acetabulum surface 618 from weight of the human patient through the contact with the artificial caput femur surface 607 by means of the supporting members 99. The prosthetic part 98 can further be fixated to the pelvic bone 9 by means of bone cement, adhesive, screws, form fitting, welding, sprints, band or some other mechanical connecting member. According to this embodiment the supporting members 99 are positioned on the acetabulum side of the pelvic bone 9, however it is also conceivable that the supporting members 99 are positioned on the abdominal side of the pelvic bone 9. The supporting means could be constructed in many different ways and this should be seen as examples.

An alternative method of creating a hole in the pelvic bone, preparing the surfaces of the caput femur and the acetabulum, inserting the positioning shaft and inserting and fixating artificial hip joint surface parts will now be described with reference to FIGS. 19-23.

Figure 19:
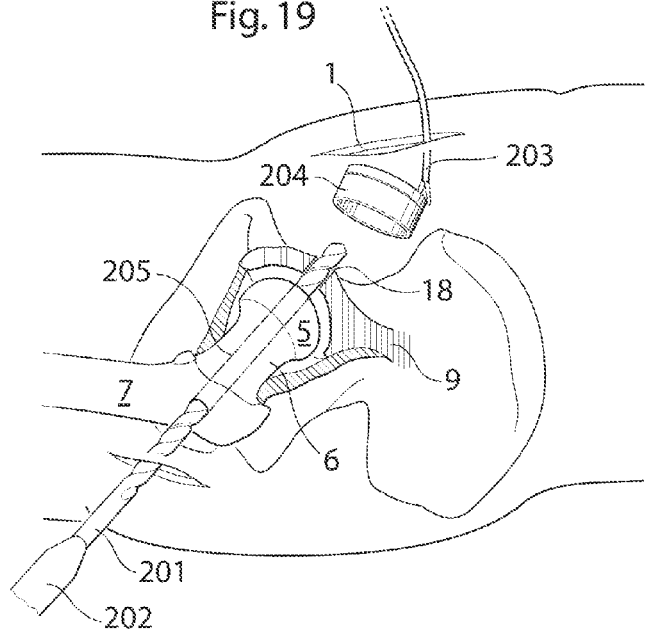
FIG. 19 shows a lateral view of the human patient when an instrument for creating a hole in the pelvic bone is provided.

FIG. 19 shows a human patient in section when an incision 1 is made in the abdominal wall of the human patient, and a second incision 200 in made in the lateral part of the left thigh. A drilling member 201 has been introduced through the incision 200 in the thigh, penetrating the fascia lata, and reaching the femoral bone 7. After the drilling member 201 has made contact with the femoral bone 7, a drilling process is started which creates a hole 205 in the cortical bone of the femoral bone 7 and into the cancellous bone of the femoral bone 7, the hole 205 then propagates along a length axis of the collum femur 6 and eventually reaches the caput femur 5, from the inside thereof. The caput femur 5 is penetrated from the inside and the drilling member 201 continues to the acetabulum 8 which is a bowled shaped part of the pelvic bone 9. The drilling member 201 penetrates the pelvic bone 9 and continues into the abdominal area of the human patient. The drilling member 201 is then retracted from the hole 205 which leaves a hole 201 reaching from the lateral side of the thigh, to the area of the hip joint. The drilling member 201 is powered by an operating device 202 which could be an electrically, hydraulically or pneumatically powered operating device 202.

After the hole 205 has been created along a length axis of the collum femur 6, a force transferring member 206 is inserted through the hole 205. The force transferring member could be a tubular or solid shaft, or a flexible member such as a wire.

Figure 20:
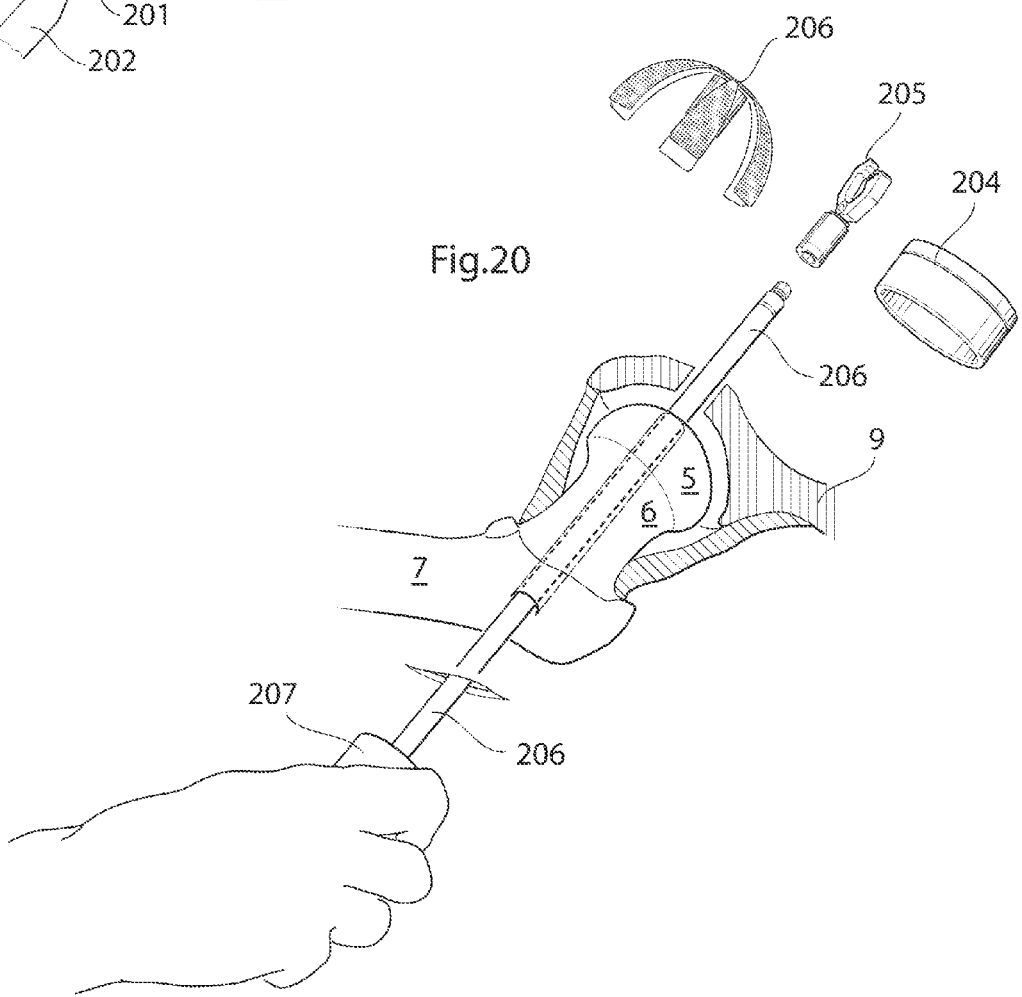
FIG. 20 shows different instruments possible to place on a force transferring member.

FIG. 20 shows the hip joint in section when a force transferring member 206 has been inserted through the hole 205. The force transferring member 206 comprises a tool fixating member 218 positioned on the end of the force transferring member 206. The tool fixating member 218 could comprise a screw-thread or a bayonet joint which could be activated to fixate a tool 224,225,226 to the force transferring member 206, by the turning of said force transferring member by means of manual manipulation or an operating device 207. FIG. 5 further shows a tool for creating a hole 224 in the pelvic bone 9, a tool 225 for manipulating an implantable device such as a prosthesis or a prosthetic part, and a tool 226 for reaming the acetabulum 8 and/or the caput femur 5. The tools comprise a fixating member 219 which acts together with the tool fixating member 218 on the force transferring member 206 to fixate the tool 224,225,226 to the force transferring member 206. The tools 224,225,226 is inserted through the incision in the abdominal region, as shown in FIG. 4. where a tool 224 for creating a hole in the pelvic bone 9 is inserted through an incision 1 in the abdominal region of the human patient using a tool introducing member 203. The force transferring member 206 according to any of the embodiments could be used as a positioning shaft, for positioning, centering and guiding a tool or a medical device, such as a prosthetic part.

Figure 21:
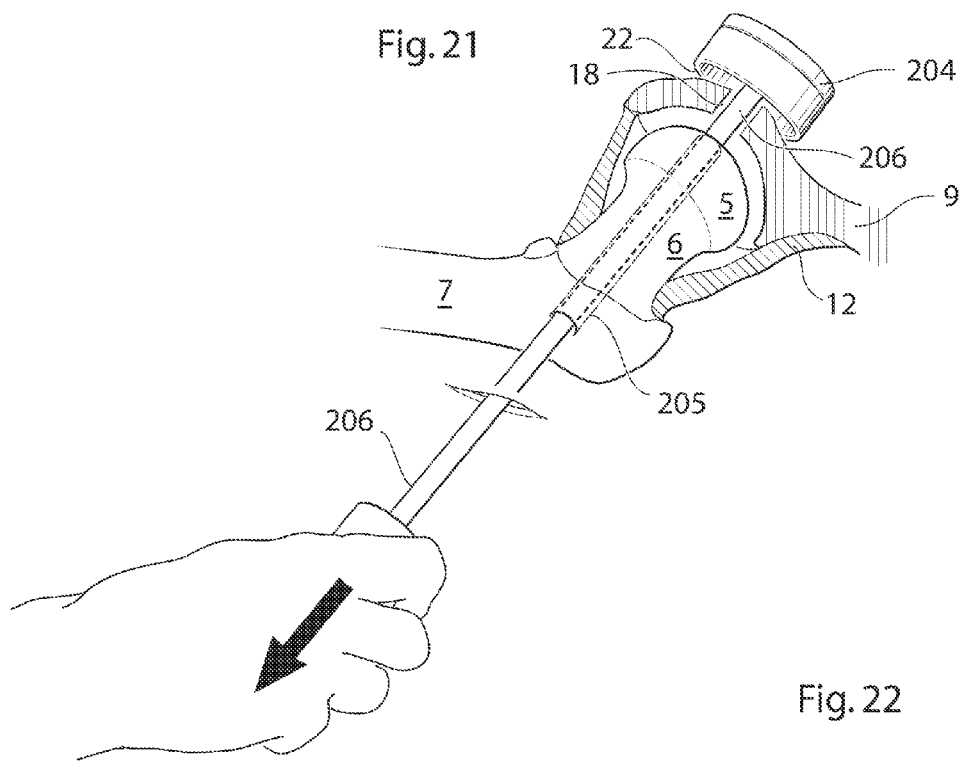
FIG. 21 shows the hip joint in section when a hole in the pelvic bone is being created.

FIG. 21 shows the hip joint in section when a tool 224 for creating a hole 18b in the pelvic bone is fixated to the tool fixating member 219 on the force transferring member 206. When the tool 224 for creating a hole in the pelvic bone 9 is applied to the force transferring member 206, the force transferring member 206 is preferably operated using an operating device 207, which could be an electrical, hydraulic or pneumatic operating device. The tool for creating a hole in the pelvic bone 9 comprises a bone contacting organ 22 which is adapted to create the hole 18b in the pelvic bone 9 through a sawing, drilling or milling process powered by a rotating, vibrating or oscillating movement of the force transferring member 206.

Figure 22:
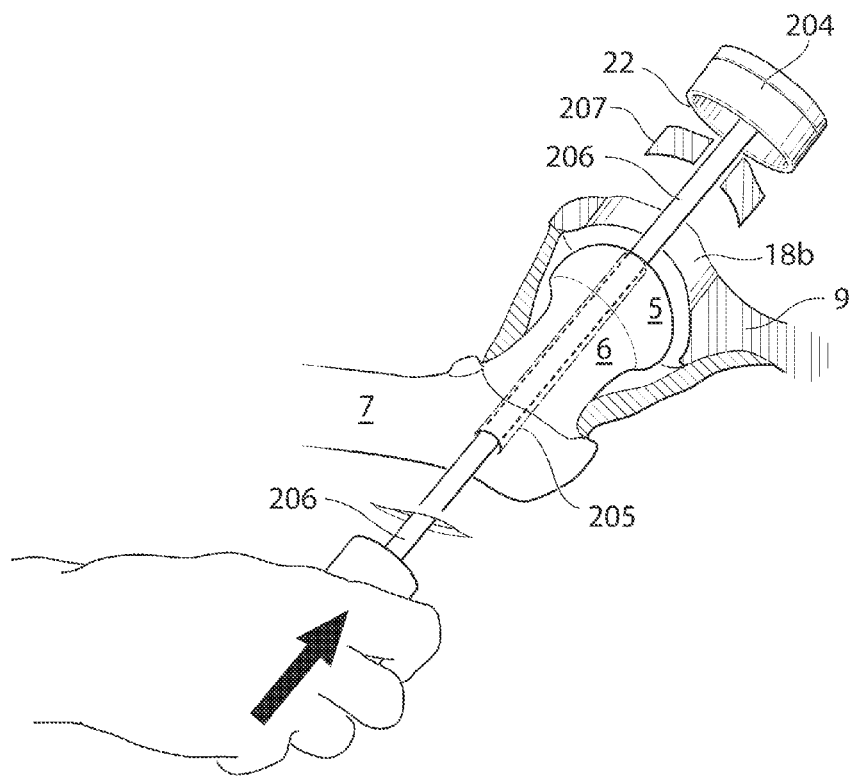
FIG. 22 shows the hip joint in section when a hole in the pelvic bone is being created.

FIG. 22 shows the hip joint in section when the hole 18b in the pelvic bone 9 has been created. According to the embodiment shown the hole 18b is created through the creation of a bone plug 207 which can be adapted to be replaced after the steps of the operation performed through the hole 18b in the pelvic bone 9 has been concluded.

Figure 23:
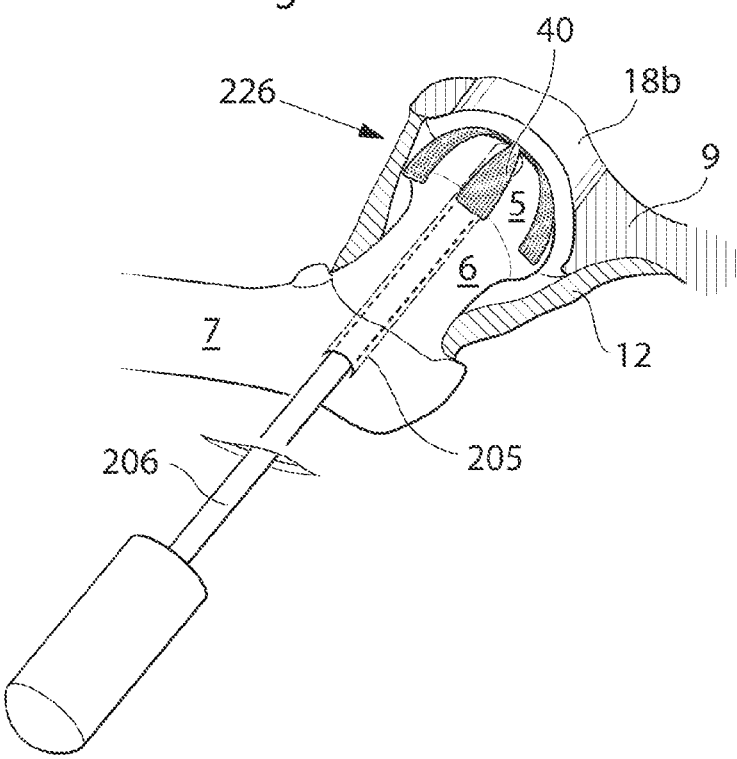
FIG. 23 shows the hip joint in section when the caput femur is being reamed.

FIG. 23 shows the reaming of the acetabulum 8 and/or the caput femur 5 using a reamer 226 comprising reaming blades 40. The reamer 226 is adapted to be introduced through the pelvic bone 9 through an incision as shown in FIG. 2. The reamer 226 is operated through manual manipulation or an operating device 207.

Figure 24A:
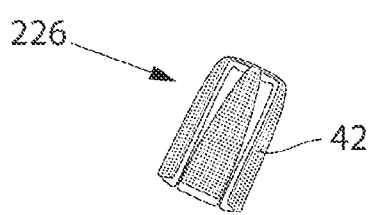
FIG. 24a-c shows the an expandable reamer.

FIG. 24a shows the reamer 226 according to an embodiment where the reamer 226 is adapted to be expandable. The reaming blades 42 are folded, which facilitates the introduction of the reamer 226 through the hole 18b in the pelvic bone 9.

Figure 24B:
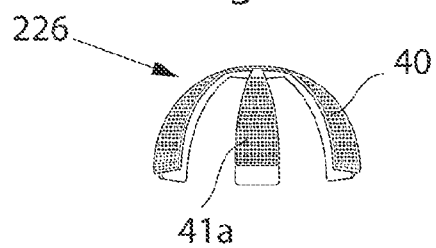

FIG. 24b shows the expandable reamer in its reaming state with the reaming blades 40 unfolded. The reaming blades 40 comprises an abrasive material which removes material, shapes and smoothens the surface of the acetabulum 8 and/or the caput femur 5. 41a denotes the abrasive material on the outside of the reaming blade 40, adapted to ream the acetabulum 8 surface.

Figure 24C:
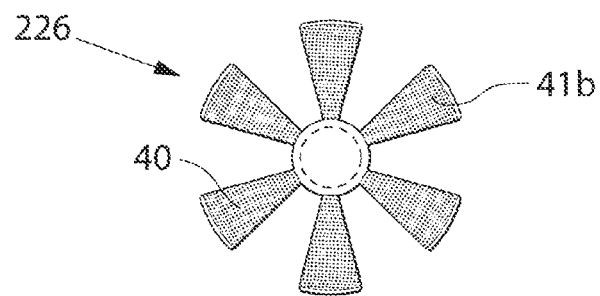

FIG. 24c shows the expandable reamer from the inside thereof, with the reaming blades 40 and the abrasive material 41b adapted to ream the caput femur 5.

After the surfaces of the caput femur 5 and/or the acetabulum 8 has been prepared the step of providing the surfaces with an artificial acetabulum surface 65 and/or an artificial caput femur surface 65 is performed.

Figure 25:
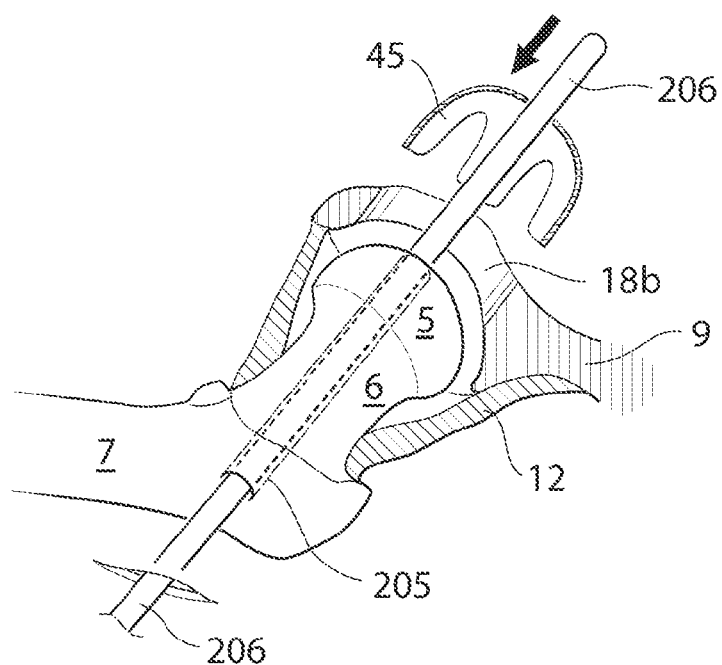
FIG. 25 shows the hip joint in section when an artificial caput femur surface is being provided.

FIG. 25 shows the step of providing an artificial caput femur surface 45 which is inserted through the incision according to FIG. 2 or FIG. 3. The artificial caput femur surface 45 is then mounted on to the force transferring member 206 which acts a guide for the surface 45, facilitating the introduction and fixation of said surface 45. However it is furthermore conceivable that the force transferring member 206 is replaced by a positioning shaft according to any of the embodiments described herein, adapted to position, center or guide the artificial caput femur surface 45 on to the caput femur 5.

An alternative way of providing an artificial hip joint surface to a surgically modified caput femur will now be described, with reference to FIGS. 26-34

Figure 26:
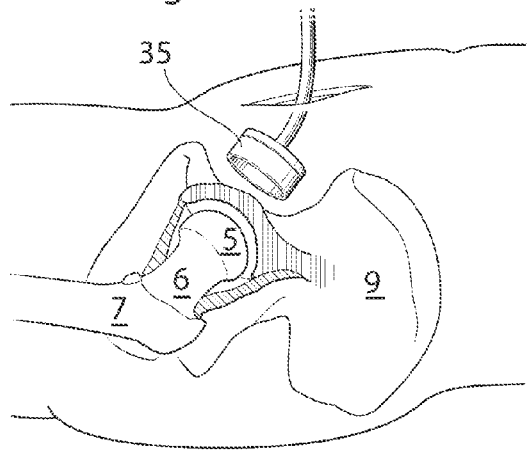
FIG. 26 shows the creation of a hole in the pelvic bone from the opposite side from acetabulum.

FIG. 26 shows a lateral view of a human patient where a surgical instrument 35 adapted to create a hole 18 in the pelvic bone 9 from the abdominal side of the pelvic bone 9 is inserted through an incision in the abdominal wall. The surgical instrument could comprises a flexible part or section 300, enabling the surgical instrument to be very precisely adjusted to reach the pelvic bone 9 or the hip joint from the abdominal side of the pelvic bone 9. The stiffness of said flexible part or section 300 could range from completely flexible to completely stiff to fit the surroundings of the particular operation. The surgical instrument 35 could be powered through an operating device which in turn could comprise an electrical, hydraulic, mechanical, pneumatic or magnetic engine and it could be adapted to create a rotating, oscillating, vibrating or repetitive movement.

Figure 27:
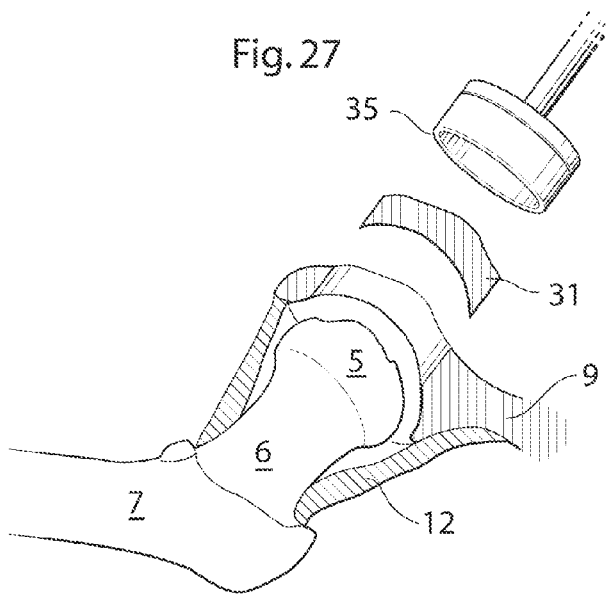
FIG. 27 shows the hip joint in section when a hole in the pelvic bone is being created.

FIG. 27 shows a hip joint in section wherein a surgical instrument 35 adapted to create a hole 18 in the pelvic bone 9 is adapted to create a bone plug 31. The bone plug 31 could be adapted to be replaced into said hole 18 after the surgical or laparoscopic steps performed in the hip joint has been concluded.

Figure 28:
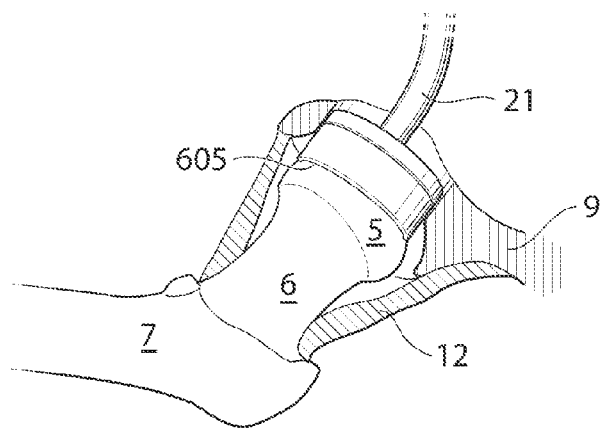
FIG. 28 shows the hip joint in section when the caput femur is being surgically modified.

FIG. 28 shows a hip joint in section wherein a surgical instrument 604 for removing the caput femur 5 is provided through a hole 18 in the pelvic bone 9. The surgical instrument comprises a sawing member 605 adapted to separate the caput femur 5 from the collum femur 6. The surgical instrument is powered through a force transferring member 21 which transfers force from an operation device or manual manipulation.

FIG. 29 shows the hip joint in section when the method of supplying a medical device is conducted according to another embodiment. The proximal part of the caput femur has been removed by the surgical instrument comprising a sawing member 605. A reaming member 40 adapted to create a concave surface 103 in the caput femur 5 is here applied to a force transferring member 206 which is inserted through a hole 205 going from the lateral side of the thigh, penetrating the cortical bone of the femoral bone 7 propagating along a length axis of the collum femur 6 in the cancellous bone and entering the area of the hip joint. The force transferring member 206 is operated using an operating device 207 which could be an electrically powered operating device, a hydraulically powered operating device or a pneumatically powered operating device. The reamer 40 is inserted into the body of the patient through an incision and placed in the hip joint through a hole 18 in the pelvic bone 9. The reaming in the caput femur and part of the collum femur 6 is mainly performed in the cancellous bone, however that does not exclude the possibility the some of the reaming needs to be performed in the cortical bone of the caput femur 5 or the collum femur 6.

FIG. 30 shows the step of applying an adhesive 106 to the concave surface created by the reamer 40. The adhesive 106 is applied by an injecting member 104 comprising an injecting nozzle 105. The adhesive 106 is preferably a biocompatible adhesive such as bone cement. The injecting member 104 is in this embodiment adapted for introduction through a hole 18 in the pelvic bone 9, through the injecting member 104 being bent.

FIG. 16 shows the step of providing a medical device 109 comprising an artificial concave hip joint surface 110. The medical device is according to this embodiment provided with a hole 905 positioned along the length axis of the collum femur 6. The medical device 109 is, through the hole 905, adapted to be guided by the positioning shaft 900 placed in the hole 902 along a length axis of the collum femur 6. The insertion of the medical device 109 into the hip joint while the positioning shaft 900 runs through the hole 905 of the medical device 109 facilitates the positioning of the medical device 109 and ensures that the different parts of the medical device 109 is centred for functioning as a unit. In the embodiment shown in FIG. 31 the medical device 109 is inserted into the hip joint as a single unit, however it is equally conceivable that the medical device 109 is inserted in parts (not shown) which are then connected to form the medical device 109 after implantation in the patient. The artificial concave hip joint surface 110 is fixated to the concave surface 103 created in the caput femur 5 and collum femur 6. The medical device 109 comprises a fixation support 111 adapted to anchor said artificial concave hip joint surface 110, to at least one of the caput femur 5 and the collum femur 6. The medical device 109 is adapted to be introduced to the hip joint through a hole 18 in the pelvic bone 9 using a manipulation device 122 comprising a gripping member 123. According to this embodiment the manipulation device 122 is bent and thereby adapted to operate through a hole 18 in the pelvic bone 9. According to one embodiment the medical device 109 comprises a self lubricating material such as PTFE, however it is also conceivable that said medical device comprises: titanium, stainless steel, corian, PE, or other acrylic polymers, in which case the medical device could be adapted to be lubricated after insertion in the hip joint.

Figure 32:
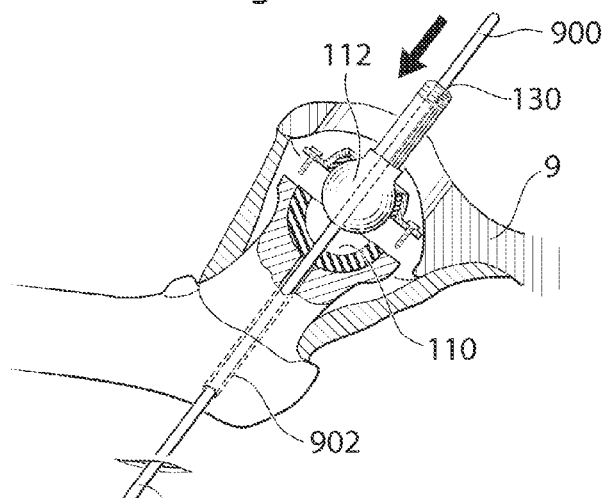
FIG. 32 shows the placing of a medical device through a hole in the pelvic bone.

FIG. 32 shows the hip joint in section when the artificial convex hip joint surface is fixated in the medical device 109 comprising a concave hip joint surface 110, the medical device 109 is positioned using the positioning shaft 900. The convex hip joint surface 112 is secured in place by the locking element 116 which is fixated to the caput femur 5 using screws 121, the convex hip joint surface is guided using the positioning shaft 900. The surface of the locking element 116 and the concave hip joint surface 110 is placed in connection with the convex hip joint surface 112 and could be made of a friction reducing material such as PTFE or a self lubricating powder material. However it is also conceivable that the connecting surfaces are lubricated using an implantable lubrication system adapted to lubricate the medical device after said medical device has been implanted in the human patient. The positioning shaft 900 assists in the centering of at least one artificial hip joint surface inside of the hip joint. According to the embodiment shown in FIG. 32 the positioning shaft 900 is inserted through the femoral bone 7, however according to other embodiments, the positioning shaft is positioned inside of the hip joint from the acetabulum side.

Figure 33:
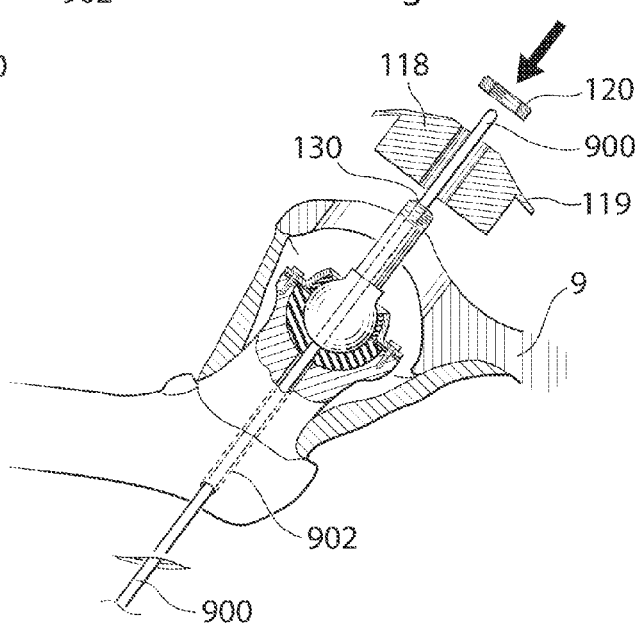
FIG. 33 shows the placing of a prosthetic part in the hole in the pelvic bone.

FIG. 33 shows the placing of a prosthetic part 118 adapted to occupy the hole 18 created in the pelvic bone 9. The prosthetic part 118 comprises supporting members 119 adapted to be in contact with the pelvic bone 9 and assist in the carrying of the load placed on the medical device from the weight of the human patient. Furthermore FIG. 33 shows the fixation of a nut 120 to the medical device, which in turn is guided by the positioning shaft 900.

Figure 34:
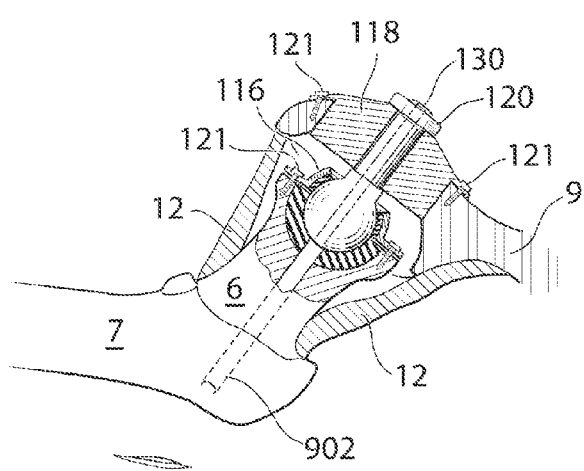
FIG. 34 shows the fixation of a prosthetic part in the hole in the pelvic bone.

FIG. 34 shows the hip joint in section when all the elements of the medical device has been fixated in the area of the hip joint or its surroundings. The prosthetic part 118 adapted to occupy the hole 18 in the pelvic bone 9 is here fixated with screws 121, however these screws 121 could be assisted or replaced by an adhesive which could be applied to the surface between the prosthetic part and the pelvic bone 9. The positioning shaft 900 has been refracted through the incision in the thigh.

Figure 35A:
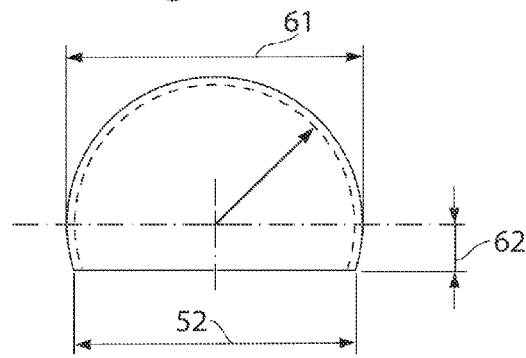
FIG. 35a shows a medical device in a schematic view.

FIG. 35a shows a schematic view of an artificial hip joint surface comprising a beyond part 62, being a part passing beyond the maximum diameter 61 of the artificial hip joint surface, thereby allowing an opening in the hip joint surface 52 to have a diameter smaller than the maximum diameter of the artificial hip joint surface.

Figure 35B:
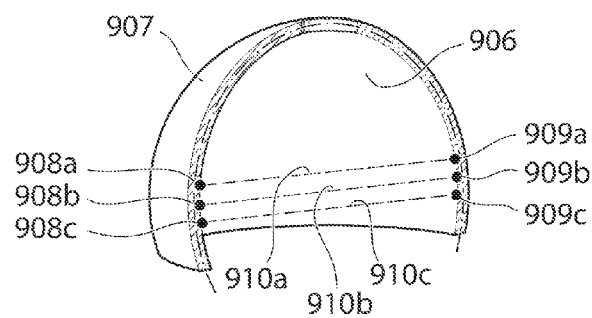
FIG. 35b shows a medical device in section.

FIG. 35b shows an artificial hip joint surface according to an embodiment where the artificial hip joint surface comprises an inner surface 906, and an outer surface 907. The inner surface has a first point 908a, a second point 909a, a third point 908b, a fourth point 909b, a fifth point 908c, and a sixth point 909c, all points located on different places along a length axis L of said inner surface 906, wherein: a first straight line 910a, reaching from said first point 908a to said second point 909a is parallel to a second straight line 910b reaching from said third point 908b to said fourth point 909b, which in turn is parallel to a third straight line 910c reaching from said fifth point 908c to said sixth point 909c, wherein: said first and said third straight lines 910a, 910c are of equal length, and wherein said second straight line 910b is longer than said first 910a and said third 910c straight lines and positioned between said first 910a and said third 910c straight lines. The artificial hip joint surface is thereby passing beyond the maximum diameter of the of the artificial hip joint surface, which enables the artificial hip joint surface to clasp an element such as the caput femur 5, an artificial caput femur surface or an artificial replacement for the caput femur.

Figure 36A:
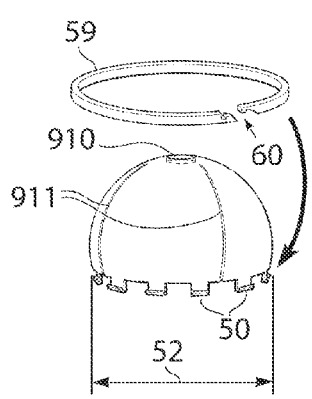
FIG. 36a shows the placing of a band onto a medical device.

FIG. 36a shows an artificial caput femur surface 45 according to an embodiment where the artificial caput femur surface is made of an expandable structure comprising multiple slits 911 adapted to enable the mounting of the artificial caput femur surface 45 on a caput femur having a largest diameter larger than the opening 52 of the artificial caput femur 45. The artificial caput femur 45 is adapted to be secured using a band 59 comprising a self locking element 60. The band 59 is adapted to encircle the artificial caput femur at the base of the artificial caput femur and to be confined by holding members 50 at the base of the artificial caput femur surface. The artificial caput femur surface 45 further comprises a positioning hole 910 adapted to surround a positioning shaft 900 adapted to guide, position and center the artificial caput femur surface 45.

Figure 36B:
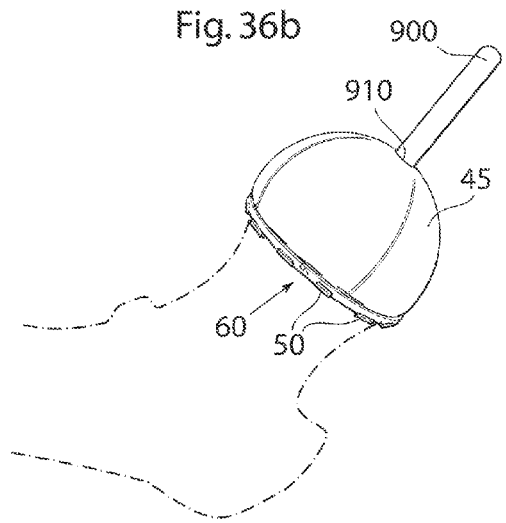
FIG. 36b shows the femoral bone when a medical device has been placed on the caput femur.

FIG. 36b shows the femoral bone 7 when the artificial caput femur surface 45 as shown in FIG. 36a has been placed on the caput femur 5, and has been secured by means of the band 60. Encircling the base of the artificial caput femur surface 45. The positioning shaft 900 is placed through the positioning hole 910 of the artificial caput femur surface 45, and the artificial caput femur surface is thereby guided, positioned and centered onto the caput femur.

FIG. 37 shows an artificial caput femur surface 45 comprising a positioning hole 910 placed centrally in the artificial caput femur surface 45. The artificial caput femur surface comprises multiple elastic arms 50 adapted to clasp the caput femur 5. The multiple elastic arms 50 have a maximum diameter 51 which is larger than the opening 52 of the artificial caput femur surface 45, which enables the artificial caput femur surface 45 to clasp the caput femur 5.

FIGS. 38a,b,c,d,e shows the artificial caput femur surface 45 according to an embodiment, in which the artificial caput femur surface 45 comprises a first 53a and a second 53b section, as shown in FIG. 38b. The first and second sections 53a,b are displaceable in relation to each other. According to a first embodiment, the first section 53a can be rotated in relation to the second section 53b, such that the second section 53b travels underneath the first section 53a to create a displaced artificial caput femur surface 54, as shown in FIG. 38c, which is possible to insert into a hip joint of a human patient through a hole 18 being oval, or at least having an area smaller than the cross sectional area of the artificial caput femur surface 45 when in its full functional size 45, as shown in FIG. 38a. According to this embodiment the two sections are connected to each other when the artificial caput femur surface 45 is returned to its full functional size using a mechanical form fitting 55, as shown in FIG. 38e. However it is also conceivable that the connection is assisted or replaced with screws, welding, sprints, band, adhesive or some other mechanical connecting member. The artificial caput femur surface further comprises a positioning hole 910 centrally placed in the artificial caput femur surface 45, and adapted to encircle a positioning shaft 900.

FIG. 39a,b shows the artificial caput femur surface 45 according to an embodiment, in which said artificial caput femur surface 45 comprises four slits. The artificial caput femur surface 45 is flexible in its construction allowing the four artificial caput femur arms 50 to be folded towards the center axis of the artificial caput femur surface 45 thus allowing the artificial caput femur surface 45 to be inserted into a hip joint through a hole smaller than the full functional size of the artificial caput femur surface 45. The artificial caput femur surface 45 according to this embodiment can be constructed to go beyond the maximum diameter of the caput femur 5, in which case the construction with the slits 49 allows the artificial caput femur surface 45 to change to both a smaller and a larger size than said full functional size. The artificial caput femur surface 45 further comprises a positioning hole 910 centrally placed in the artificial caput femur surface 45, and adapted to encircle a positioning shaft 900.

FIG. 39b shows the artificial caput femur surface 45 in section when said artificial caput femur surface arms 50 are folded for insertion through a hole 18 with an area smaller than the largest area of the artificial caput femur surface 45 when in its full functional size.

Figure 40A:
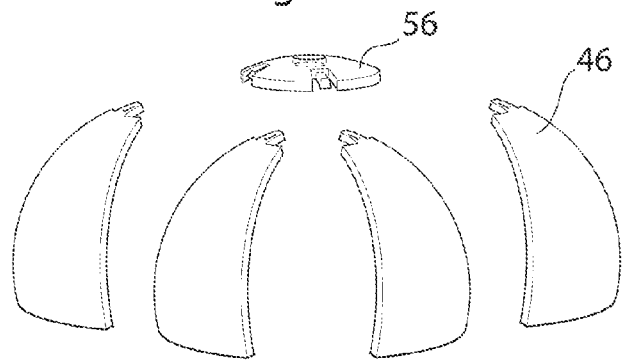
FIG. 40a shows the medical device in an embodiment where the medical device comprises multiple parts.
Figure 40B:
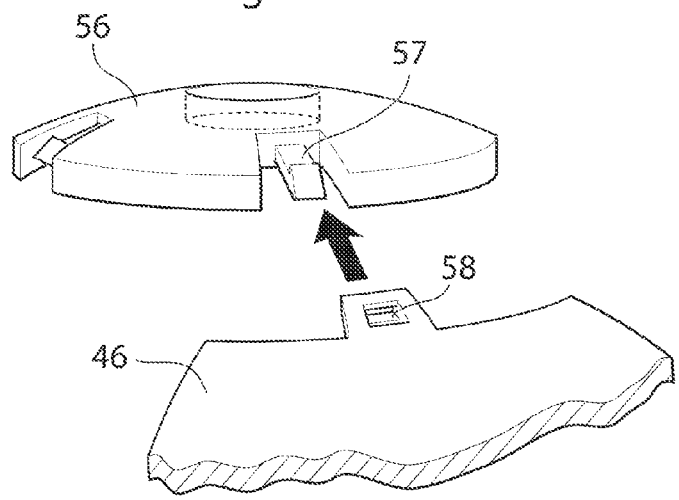
FIG. 40b shows the medical device in an embodiment where the medical device comprises multiple parts, in greater detail.
Figure 40C:
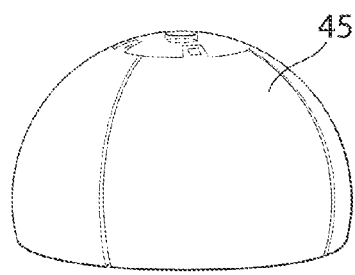
FIG. 40c shows the medical device in an embodiment where the medical device comprises multiple parts, when assembled.

FIG. 40a,b,c shows the artificial caput femur surface 45 according to an embodiment, in which the artificial caput femur surface 45 comprises multiple artificial caput femur surface parts 46. The multiple artificial caput femur surface parts 46 are adapted to be connected to an interconnecting artificial caput femur surface part 56 after insertion into a hip joint. The interconnecting artificial caput femur surface part 56 comprises self locking connecting members 57, shown in FIG. 40b, that fits with corresponding self locking members 58 of the artificial caput femur surface parts 46. The artificial caput femur surface parts 46 create an artificial caput femur surface 45 when connected to each other, shown in FIG. 40c. The self locking members 57, 58 can be assisted or replaced with screws, welding, sprints, band, adhesive or some other mechanical connecting member. The artificial caput femur surface 45 according to this embodiment can further be adapted to go beyond the maximum diameter of the caput femur 5. The artificial caput femur surface 45 further comprises a positioning hole 910 centrally placed in the artificial caput femur surface 45, and adapted to encircle a positioning shaft 900.

The embodiments above have been discussed in relation to an artificial caput femur surface, however it is equally conceivable that the technical solutions presented in the embodiments are used for artificial acetabulum surfaces, which can be used on their own or in connection with an artificial caput femur surface.

FIG. 41 shows an artificial acetabulum surface 65 according to an embodiment, in which the artificial acetabulum surface 65 comprises at least one slit 66 enabling the artificial acetabulum surface 65 to vary in size for insertion through a hole smaller than the full functional size of the artificial acetabulum surface 65. The slits are placed between one or more artificial caput femur surface arms 67 which are flexible by means of the material or by means of a joint affecting the artificial acetabulum surface arms 67. The artificial acetabulum surface comprises a positioning hole 910 placed centrally in the artificial acetabulum surface 65 and adapted to guide, center and position the artificial acetabulum surface 65 in the hip joint in combination with an artificial caput femur surface 45 according to any on the embodiments above, or an artificial replacement for the entire caput femur.

FIG. 42a shows the femoral bone where multiple positioning shafts 900a,b,c are placed in the caput femur 5. The positioning shafts 900a,b,c are adapted to guide, position and center artificial hip joint surface parts 913a,b on to the caput femur 5, or guide, position and center artificial hip joint surface parts 913a,b to be placed in the acetabulum. The artificial hip joint surface parts 913a,b each have a positioning hole 910a,b which are adapted to encircle the positioning shafts 900a,b,c placed in the caput femur 5. The artificial hip joint surface parts 913a,b are adapted to be connected to each other after insertion the hip joint using mechanical connecting members 914a,b, wherein the mechanical connecting members comprises a first part 914a placed in a first artificial hip joint surface part 913b and adapted to fit in a corresponding second part 914b, placed in a second artificial hip joint surface part 913a. The multiple positioning shafts 900a,b thereby assists in the connection of multiple artificial hip joint surface parts 913a,b to each other. However the mechanical connecting members 914a,b could be assisted or replaced by an adhesive.

FIG. 42b shows the positioning of the artificial hip joint surface parts 913a,b from above with the positioning holes 910a,b of the artificial hip joint surface parts 913a,b encircling the positioning shafts 900a,b,c and thereby the positioning shafts 900a,b,c guiding, positioning and centering the artificial hip joint surface parts 913a,b in the hip joint.

FIG. 43a shows a tool for placing multiple positioning shafts 900a,b,c in the caput femur 5. The tool comprises the positioning shafts 900a,b,c which each comprise a drilling member 916 placed in the distal ends of the positioning shafts 900a,b,c. The drilling members 916 are adapted to penetrate the surface and the cortical bone of the caput femur, and enter the cancellous bone of the collum femur 6, thereby creating holes in which the positioning shafts 900a,b,c can be placed. The positioning shafts 900a,b,c of the tool are connected to a base part 917 which serves as transmission from an operation device 915, for supplying all of the drilling members 916 with force transferred over the positioning shafts 900a,b,c for creating the holes in the caput femur 5.

FIG. 43b shows the tool from above where the positioning shafts 900a,b,c are operably connected to each other through driving elements 918, connected to the operation device 915. The driving elements 918 and the positioning shafts 900a,b,c are operably connected to the base part 917 making up the foundation of the tool.

In embodiments where a hole 18 has been made in the pelvic bone 9 for introduction of medical devices according to any of the embodiments above, it is necessary to close the hole 18 in the pelvic bone 9 using a bone plug or prosthetic part. The process and embodiments of the bone plug or prosthetic part will now be described.

FIG. 44a shows a prosthetic part 98 being inserted into a hole 18 in the pelvic bone 9 from the opposite side from acetabulum 8. According to one embodiment the prosthetic part 98 comprises supporting members 99 adapted to correspond with sections 100 of the hole 18 in the pelvic bone 9. After the prosthetic part 98 has been inserted into said hole 18 in the pelvic bone 9 it is rotated so that the supporting members 99 comes in contact with the pelvic bone 9 and can carry the load placed on the acetabulum 8 from weight of the human patient through the contact with the caput femur 5. Said prosthetic part 98 could also be adapted to serve as artificial acetabulum surface 65 according to any of the above mentioned embodiments. The prosthetic part comprises a positioning hole 910 placed centrally in the prosthetic part 98 for guiding, positioning and centering the prosthetic part in the hole 18 in the pelvic bone 9 and/or in relation to an artificial caput femur surface and/or an artificial acetabulum surface. The positioning hole 910 encircles a positioning shaft 900 placed in the caput femur 5.

FIG. 44b shows the prosthetic part 98 when rotated to carry the load placed on the acetabulum 8 from weight of the human patient through the contact with the caput femur 5.

FIG. 45 shows the hip joint of a human patient in section wherein the prosthetic part 98 closes the hole 18 in the pelvic bone 9 and carries the load placed on the acetabulum 8 from weight of the human patient through the contact with the caput femur 5 by means of the supporting members 99. The prosthetic part 98 can further be fixated to the pelvic bone 9 by means of bone cement, adhesive, screws, form fitting, welding, sprints, band or some other mechanical connecting member. According to the embodiment of FIG. 45, a positioning shaft is placed in the collum femur from the lateral side of the thigh, penetrating a hole 902 in the femoral bone 7, the collum femur 6 and the caput femur 5 and entering through a hole 18 in the pelvic bone 9 and into the abdomen, for guiding, positioning and centering medical devices, such as a prosthetic part as shows in FIG. 44a,b, comprising a positioning hole 910, in the hip joint.

FIG. 46 shows the hip joint of a human patient in section wherein bone plug 31 or prosthetic part 98 is attached to the pelvic bone 9 by means of screws 101 placed from the opposite side from acetabulum 8. The screws 101 are possible to place in different angles depending on reach or need for support. The positioning shaft 900 has been retracted from the hole 902 in the femoral bone 7 the collum femur 6 and the caput femur 5, and a smaller hole 18b in the bone plug 207.

Figure 47:
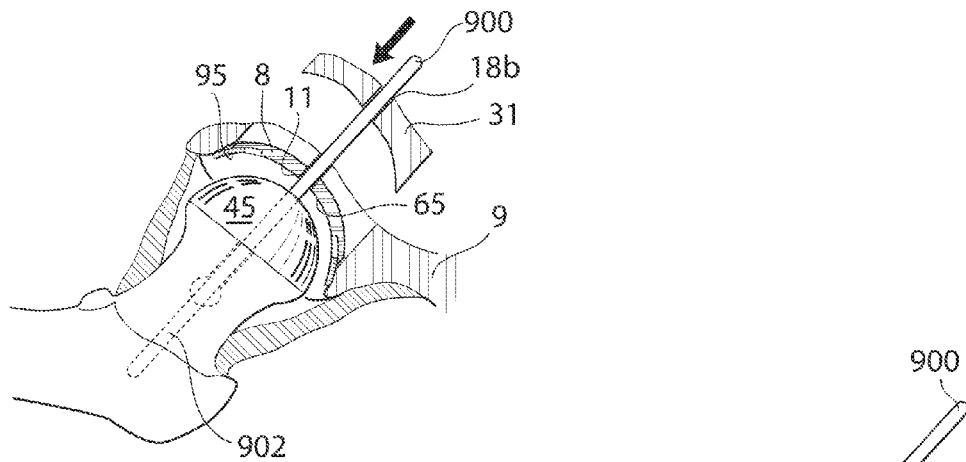
FIG. 47 shows the hip joint in section when a bone plug is being provided.

FIG. 47 shows the hip joint of a human patient in section wherein a bone plug 31 is placed in the hole 18 in the pelvic bone 9 to close the hole 18. According to a first embodiment the artificial acetabulum surface 65 comprises supporting members 95 which carries the load placed on the acetabulum 8 from weight of the human patient through the contact with the caput femur 5. The supporting members 95 can be adapted to be displaceable 97 supporting members. The bone plug 31 can be attached to the artificial acetabulum surface 11 and/or the pelvic bone 9 by means of bone cement, adhesive, screws, form fitting, welding, sprints, band or some other mechanical connecting member. According to the embodiment shown in FIG. 47 an artificial caput femur surface 45 and an artificial acetabulum surface 65 has been provided, guided, positioned and centered by a positioning shaft 900 placed in a hole 902 in the collum femur 6 and the caput femur 5. The bone plug 31 also comprises a positioning hole 18b, centrally placed, for guiding, positioning and centering the bone plug 31 for closing the hole 18 in the pelvic bone 9.

Figure 48:
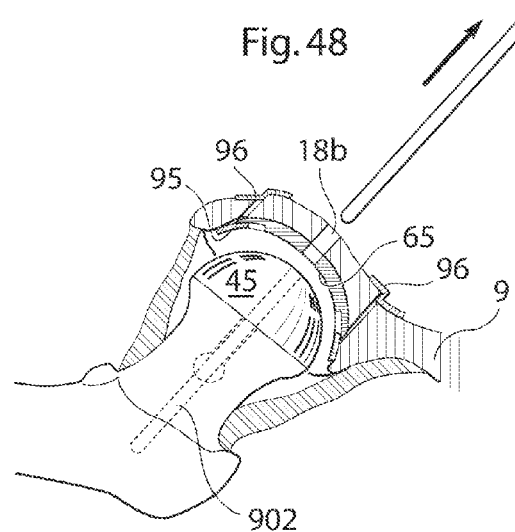
FIG. 48 shows the removal of the positioning shaft from the hip joint.

FIG. 48 shows the hip joint of a human patient in section wherein the bone plug 31 placed in the hole 18 in the pelvic bone 9 is further supported by supporting means 96 placed between the bone plug 31 and the pelvic bone 9 on the opposite side from acetabulum 8 using at lest one of: bone cement, adhesive, screws, form fitting, welding, sprints, band or some other mechanical connecting member. The positioning shaft 900 is retracted from the hole 902 in the caput femur 5 and the collum femur 6, and the hole in 18b in the bone plug 31 after the guiding, positioning and centering of the medical devices in the hip joint is concluded.

Figure 49:
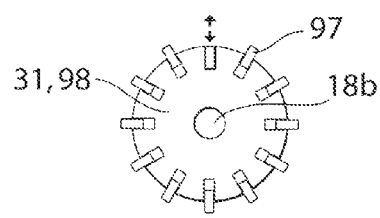
FIG. 49 shows a prosthetic part, in further detail.

FIG. 49 shows a bone plug 31 or a prosthetic part 98 comprising several displaceable supporting members 97 adapted to carry the load placed on the acetabulum 8 from weight of the human patient through the contact with the caput femur 5. The displaceable parts 97 are displaced into a corresponding part in or at the edge of the hole 18 in the pelvic bone 9.

This supporting means could be constructed in many different ways and this should be seen as examples.

Figure 50:
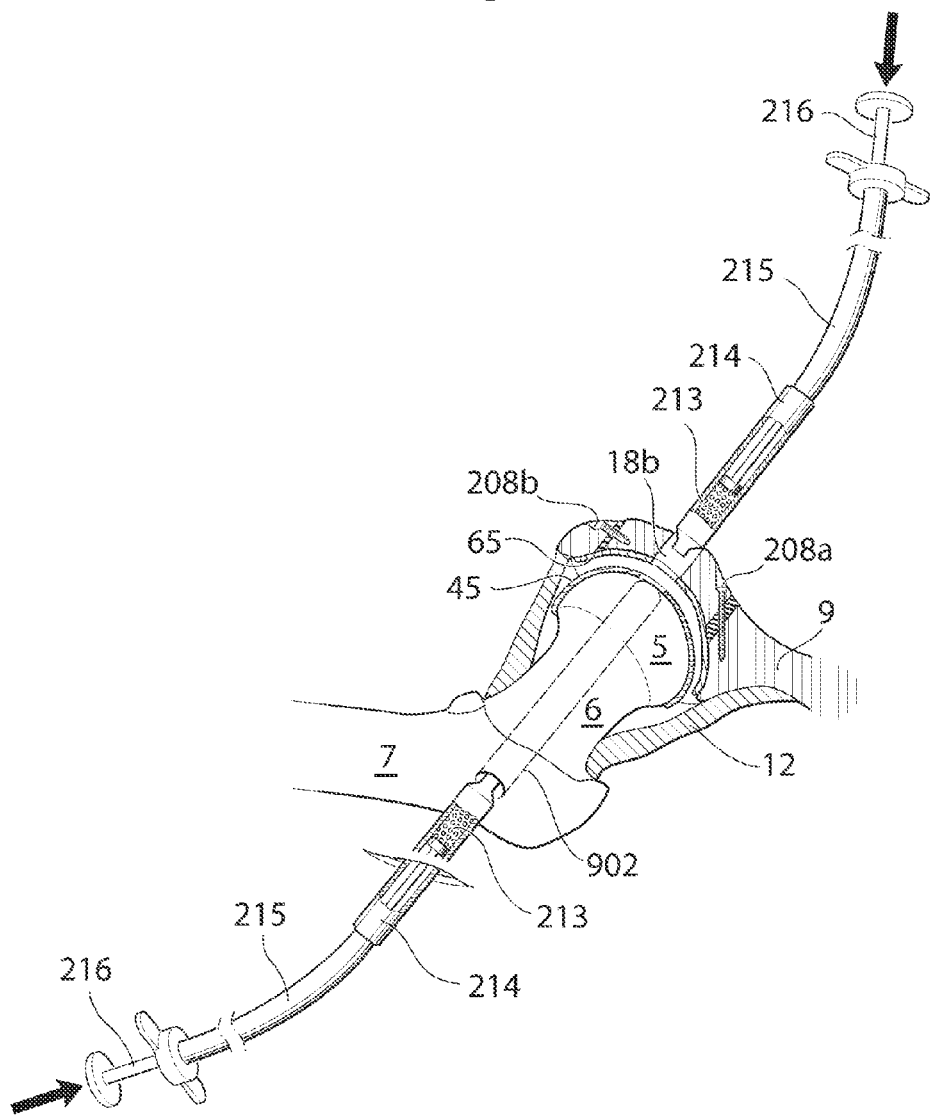
FIG. 50 shows injecting members injecting material into the holes in the femoral bone and the pelvic bone.

FIG. 50 shows the step of filling the hole 902 created in the femoral bone 7 and/or the collum femur 6 and/or the caput femur 5 and/or the hole in the pelvic bone 18b. The injecting members 214 is adapted to inject a fluid 213 into the holes 902, 18b, the fluid 213 could be bone cement or another biocompatible fluid adapted to harden. The injecting members 214 comprises a piston 216 which transfers force through a force transferring member 215 which could be flexible for facilitating the surgeon reaching the area where the holes 902, 18b is located. After the step of injecting a fluid 213 adapted to harden into the hole 205 is concluded the instruments used in the surgical or laparoscopic method is retracted and the tissue is closed in layers.

FIG. 51 shows an implantable lubrication system 920 which is adapted to lubricate the artificial hip joint surfaces after implantation in the patient. The lubrication system 920 is adapted to lubricate the artificial hip joint surfaces intermittently, continuously or as a response to a sensor signal. The lubrication system comprises a reservoir 924 adapted to hold the lubricating fluid 926. The reservoir is in fluid connection to an injection port 922, implanted subcutaneously in the patient. According to the embodiment shown in FIG. 51 the reservoir is spring loaded using a spring 925 placed in the reservoir and affecting a moveable wall portion, thereby placing a pressure on the lubricating fluid 926 inside of the reservoir 924. The lubricating system 920 further comprises control logic 923 for controlling the lubricating process by an input from the patient, e.g. through a wireless remote control, or through a sensor input, the sensor preferably sensing the state of lubrication in the hip joint, or through a timing device for intermittently lubricating the hip joint. The lubricating fluid 926 is transferred to the hip joint through a lubricating fluid transferring member 921 placing the area of the hip joint in which the lubricating fluid 926 should be applied, in fluid connection with the implanted reservoir 924. The injection port 922 is placed subcutaneously in the patient and the entire implantable lubrication system is preferably fixated to the muscular tissue of the abdomen 927, through in outer part 930 and an inner part 931 clamping the muscular tissue 927.

Figure 52A:
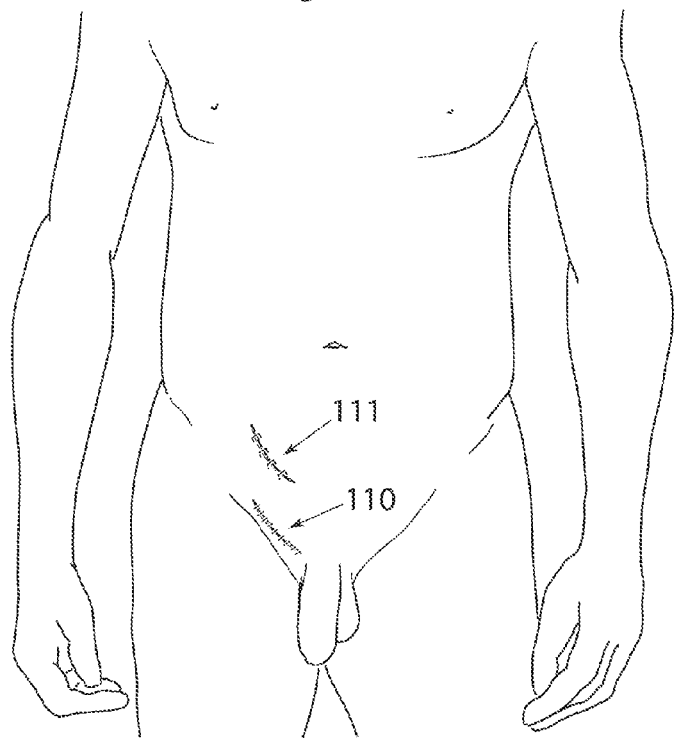
FIG. 52a shows a frontal view of the human patient when sutures or staplers are being provided.
Figure 52B:
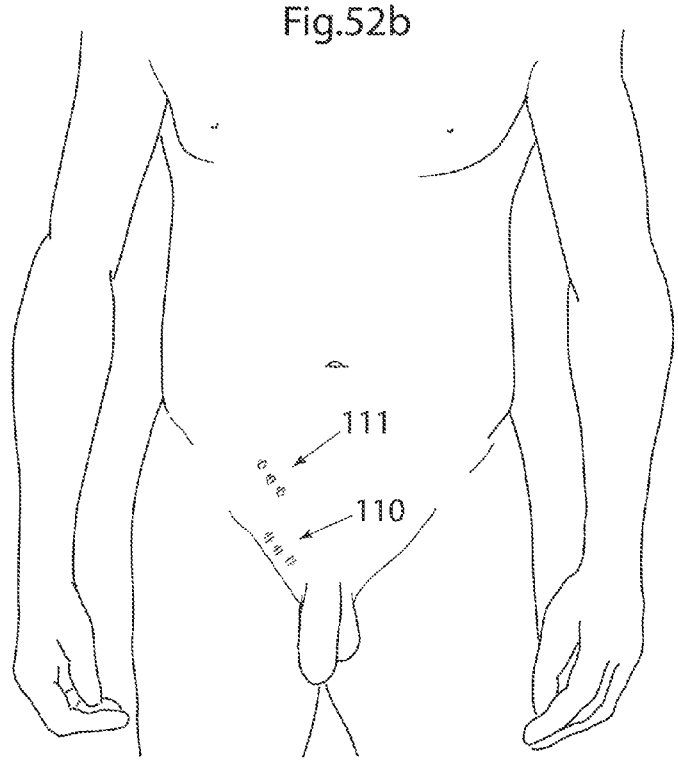
FIG. 52b shows a frontal view of the human patient when sutures or staplers are being provided.

FIG. 52*a* shows the step of suturing 110 or stapling 111 the skin 106 of the human patient in the surgical method, whereas FIG. 52*b* shows the step of suturing 110 or stapling 111 the skin 106 of the human patient in the laparoscopic method.

Please note that any embodiment or part of embodiment as well as any method or part of method could be combined in any way. All examples herein should be seen as part of the general description and therefore possible to combine in any way in general terms. Please note that the description in general should be seen as describing both of an apparatus and a method.

The invention claimed is:

1. An implantable medical device for implantation in a hip joint of a human patient, the hip joint comprising a caput femur shaped like a ball, being connected to a collum femur and being the upper extremity of a femoral bone, the collum femur and caput femur having a longitudinal axial distribution with a longitudinal caput femur centre axis reaching from the collum femur, in the centre of the collum femur and caput femur and towards an acetabulum, the acetabulum is a bowl shaped section of the pelvic bone, with an opening towards the caput femur, the acetabulum having an acetabulum centre axis reaching from the centre of the bottom of the bowl towards the centre of the opening and the normal position of the caput femur, wherein the caput femur centre axis is aligned with the acetabulum centre axis in a special centered position, when the caput femur is aligned, centered and symmetrical in the acetabulum, the caput femur and acetabulum each having a hip joint carrying surface, facing each other and contacting each other, the hip joint carrying surfaces, carrying weight in the hip joint, wherein said medical device comprises:

an artificial caput femur or an artificial caput femur surface comprising a positioning through-hole having at least one opening, said positioning through-hole being adapted to receive a positioning shaft, wherein the positioning through-hole is adapted to at least partly surround the shaft, for positioning said artificial caput femur or artificial caput femur surface in a desired position in the hip joint, an artificial acetabulum or an artificial acetabulum surface comprising a positioning through-hole having at least one opening, said positioning through-hole being adapted to receive a positioning shaft, wherein the positioning through-hole is adapted to at least partly surround the shaft, for positioning said at least one artificial hip joint surface in a desired position in the hip joint, and a stiff positioning shaft adapted to be placed in a bore in at least one of the femoral bone and the pelvic bone, and adapted to penetrate the positioning through-holes of the artificial caput femur or the artificial caput femur surface or the artificial acetabulum or the artificial acetabulum surface, for positioning said artificial caput femur or artificial caput femur surface in relation to said artificial acetabulum or artificial acetabulum surface and in relation to the femoral bone and/or the pelvic bone.

2. The implantable medical device according to claim 1, the caput femur having a substantially ball shaped configuration with a maximum diameter substantially perpendicular to the caput femur centre axis, wherein said artificial caput femur surface comprises an inner surface and at least one first beyond part of said artificial caput femur surface adapted to cover and/or go into the bone of the caput femur on at least a part of the caput femur beyond the maximum diameter of the caput femur along the caput femur center axis, away from the acetabulum cup towards said collum femur, when mounted on the caput femur in its functional position in the joint, said at least one first beyond part is adapted to have a distance perpendicular to said caput femur centre axis, being smaller than maximum distance from said inner surface of the artificial caput femur surface to said centre axis, perpendicular to said artificial caput femur surface to said centre axis, said medical device thus being adapted to create a more stable position of said artificial caput femur surface when mounted on the caput femur in said functional position.

3. The implantable medical device according to claim 1, wherein said artificial caput femur or artificial caput femur surface and the artificial acetabulum or artificial acetabulum surface has a largest diameter or a largest cross-sectional distance, and wherein said largest diameter or cross sectional distance is adapted to be changed during an operation.

4. The implantable medical device according to claim 1, wherein said artificial acetabulum or artificial acetabulum surface are adapted to be in movable connection with said artificial caput femur or artificial caput femur surface when implanted in the hip joint.

5. The implantable medical device according to claim 1, wherein said medical device is adapted to be fixated to at least one of the caput femur, the collum femur and the femoral bone using a fixation element.

6. The implantable medical device according to claim 5, wherein said fixation element is a fixation element selected from a group consisting of:
- at least one screw,
- at least one pin,
- at least one portion of at least one of the parts adapted to be introduced into the other part,
- the parts being adapted to be sliding into the other part,
- form fitting,
- welding,
- adhesive,
- pin,
- wire,
- a ball mounted into a bowl being portions of said parts,
- a male portion of one part mounted into a female portion of the other part,
- a key introduced into a lock being portions of said parts,
- band, and
- other mechanical connecting members.

7. The implantable medical device according to claim 1, wherein said artificial acetabulum surface comprises an artificial convex hip joint surface adapted to be fixated to the pelvic bone.

8. The implantable medical device according to claim 1, wherein said artificial acetabulum surface has a largest diameter or a largest cross-sectional distance, and an opening, and wherein said largest diameter or cross sectional distance is adapted to be changed during an operation.

9. The implantable medical device according to claim 1, wherein at least one of the positioning hole of the artificial caput femur or artificial caput femur surface and the positioning hole of the artificial acetabulum or artificial acetabulum surface is substantially circular.

10. The medical device according to claim 1, wherein the caput femur has a convex hip joint surface towards the center of the hip joint, and the acetabulum, has a concave hip joint surface towards the center of the hip joint, wherein the artificial caput femur or an artificial caput femur surface, having a convex shape towards the center of the hip joint, comprising the first hole and the artificial acetabulum or an artificial acetabulum surface, having a concave shape towards the center of the hip joint, comprising the second hole, wherein at least one of said artificial caput femur or said artificial caput femur surface and said artificial acetabulum or said artificial acetabulum surface are adapted to be centered in the hip joint by said positioning shaft placed in said hole and in at least one of the femoral bone and the pelvic bone, wherein said artificial convex caput femur or said artificial convex caput femur surface has said first hole placed in said convex part, for enabling the positioning shaft to be introduced into said hole and centering said artificial convex caput femur or said artificial convex caput femur surface, when placed in the hip joint, and said artificial concave acetabulum or said artificial concave acetabulum surface has said second hole placed in said concave part, for enabling the positioning shaft to be introduced into said hole and centering said artificial concave acetabulum or said artificial concave acetabulum surface, when placed in the hip joint, when said hip joint is placed in a centered position.

11. The medical device according to claim 1, wherein at least one of the artificial caput femur or artificial caput femur surface and the artificial acetabulum or artificial acetabulum surface has a through going hole with an hole inlet and an hole outlet, said hole being adapted to receive the positioning shaft into said hole inlet and passing out from the hole outlet.

* * * * *